(12) United States Patent
Sabater et al.

(10) Patent No.: US 12,090,262 B2
(45) Date of Patent: Sep. 17, 2024

(54) DEVICE AND SYSTEM FOR INJECTING BIOLOGICAL TISSUE

(71) Applicants: TissueCor, LLC, Miami, FL (US); University of Miami, Coral Gables, FL (US)

(72) Inventors: Alfonso L. Sabater, Miami, FL (US); William B. Buras, Miami, FL (US); Alejandro M. Sabater, Miami, FL (US); Daniel J. Duminuco, Holtsville, NY (US); Michael A. Botta, Ridge, NY (US)

(73) Assignees: TissueCor, LLC, Miami, FL (US); University of Miami, Coral Gables, FL (US)

( * ) Notice: Subject to any disclaimer, the term of this patent is extended or adjusted under 35 U.S.C. 154(b) by 0 days.

(21) Appl. No.: 17/464,529

(22) Filed: Sep. 1, 2021

(65) Prior Publication Data

US 2023/0060227 A1 Mar. 2, 2023

(51) Int. Cl.
*A61M 1/00* (2006.01)

(52) U.S. Cl.
CPC .............. *A61M 1/842* (2021.05); *A61M 1/87* (2021.05); *A61M 2210/0612* (2013.01)

(58) Field of Classification Search
CPC .... A61F 2/1691; A61F 2/0095; A61F 2/1662; A61F 2/1667; A61F 2/148; A61F 9/007; A61F 9/00736–00763; A61M 5/345; A61M 2005/342; A61M 5/344; A61M 5/346; A61M 1/842; A61M 1/87
See application file for complete search history.

(56) References Cited

U.S. PATENT DOCUMENTS

| | | |
|---|---|---|
| 1,704,921 A | 3/1929 | Nicoll |
| 2,853,070 A | 9/1958 | Maurice |
| 2,903,794 A | 9/1959 | Carfagni |
| 3,738,006 A | 6/1973 | Lopez et al. |

(Continued)

FOREIGN PATENT DOCUMENTS

| | | | |
|---|---|---|---|
| DE | 202011106789 U1 | 11/2011 | |
| EP | 3162401 A2 * | 5/2017 | ............ A61M 5/001 |

(Continued)

OTHER PUBLICATIONS

International Search Report for copending PCT/IB2022/058183, mailed Mar. 2, 2023 (6 pages).

*Primary Examiner* — Rebecca E Eisenberg
*Assistant Examiner* — Linnae E. Raymond
(74) *Attorney, Agent, or Firm* — Koenig IP Works, PLLC; Katherine Koenig

(57) ABSTRACT

A device, kit, and method for aspirating graft tissue and delivering the graft tissue to a target delivery site. An injector comprises a cylinder and a plunger that is both linearly and rotatably advanceable and retractable within the cylinder. A kit comprises an injector, a cartridge, and a cartridge coupling element that connects the cartridge to the injector. The kit may also include a container that is configured to retain a cartridge and to facilitate connection between the injector and the cartridge. The container includes at least one fluid barrier that prevents spillage of storage solution from the container when the injector is at least partially inserted into the well of the container.

13 Claims, 13 Drawing Sheets

(56) References Cited

U.S. PATENT DOCUMENTS

| | | | |
|---|---|---|---|
| 4,795,444 A | 1/1989 | Hasegawa et al. | |
| 5,336,088 A | 8/1994 | Discko, Jr. | |
| 5,722,971 A | 3/1998 | Peyman | |
| 5,964,748 A | 10/1999 | Peyman | |
| 6,019,765 A | 2/2000 | Thornhill et al. | |
| 6,203,538 B1 | 3/2001 | Peyman | |
| 6,217,571 B1 | 4/2001 | Peyman | |
| 6,221,067 B1 | 4/2001 | Peyman | |
| 6,280,470 B1 | 8/2001 | Peyman | |
| 8,029,515 B2 | 10/2011 | Shiuey | |
| 8,673,002 B2 | 3/2014 | Walter et al. | |
| 9,326,847 B2 | 5/2016 | Sanger | |
| 9,999,497 B2 | 6/2018 | Shiuey | |
| 10,041,865 B2 | 8/2018 | Tran | |
| 10,085,887 B2 | 10/2018 | Donitzky et al. | |
| 10,130,511 B2 | 11/2018 | Dantus | |
| 10,335,556 B2 * | 7/2019 | Vedrine | A61M 5/3134 |
| 11,311,680 B2 * | 4/2022 | Okihara | A61M 5/19 |
| 2001/0027314 A1 | 10/2001 | Peyman | |
| 2004/0122438 A1 | 6/2004 | Abrams | |
| 2008/0281341 A1 | 11/2008 | Miller et al. | |
| 2009/0069817 A1 | 3/2009 | Peyman | |
| 2010/0057093 A1 | 3/2010 | Ide et al. | |
| 2010/0069915 A1 | 3/2010 | Shiuey | |
| 2010/0211051 A1 | 8/2010 | Weston et al. | |
| 2012/0059488 A1 | 3/2012 | Shimmura | |
| 2012/0123533 A1 | 5/2012 | Shiuey | |
| 2012/0226286 A1 | 9/2012 | Weston et al. | |
| 2013/0085567 A1 | 4/2013 | Tan et al. | |
| 2013/0274875 A1 | 10/2013 | Ide et al. | |
| 2013/0317605 A1 | 11/2013 | Ide et al. | |
| 2013/0331870 A1 | 12/2013 | Hargis | |
| 2014/0221822 A1 | 8/2014 | Ehlers et al. | |
| 2014/0288643 A1 | 9/2014 | Torres et al. | |
| 2015/0297340 A1 | 10/2015 | Esguerra et al. | |
| 2016/0270904 A1 | 9/2016 | Neusidl | |
| 2017/0079838 A1 * | 3/2017 | Nishida | A61F 9/0017 |
| 2017/0128263 A1 | 5/2017 | Maminishkis | |
| 2017/0258633 A1 | 9/2017 | Vure et al. | |
| 2017/0340428 A1 | 11/2017 | Szurmann et al. | |
| 2018/0106704 A1 | 4/2018 | Tran | |
| 2018/0143109 A1 | 5/2018 | Tran | |
| 2018/0220884 A1 | 8/2018 | Joo et al. | |
| 2018/0263756 A1 | 9/2018 | Shiuey | |
| 2018/0311027 A1 * | 11/2018 | Distefano | A61B 50/20 |
| 2019/0038400 A1 | 2/2019 | Samudre | |
| 2019/0060054 A1 | 2/2019 | Balachandran | |
| 2019/0125520 A1 | 5/2019 | Bachmann et al. | |
| 2019/0159931 A1 | 5/2019 | Balachandran | |
| 2019/0223997 A1 | 7/2019 | Nun et al. | |
| 2019/0224002 A1 * | 7/2019 | Springer | A61F 2/1678 |
| 2019/0269826 A1 | 9/2019 | Peyman | |
| 2019/0380870 A1 | 12/2019 | Lue et al. | |
| 2020/0015959 A1 * | 1/2020 | Wensrich | A61F 2/1672 |
| 2020/0276010 A1 | 9/2020 | Sabater et al. | |
| 2021/0069426 A1 | 3/2021 | Huculak et al. | |
| 2021/0244530 A1 * | 8/2021 | El-Ayari | A61F 2/0095 |
| 2022/0176043 A1 * | 6/2022 | Wang | A61M 5/31511 |
| 2023/0014433 A1 * | 1/2023 | Abdullayev | A01N 1/0263 |

FOREIGN PATENT DOCUMENTS

| | | | |
|---|---|---|---|
| EP | 3698758 A1 | 8/2020 | |
| FR | 2720279 A1 * | 12/1995 | A61M 5/5066 |
| WO | WO-2008156036 A1 * | 12/2008 | A61M 5/346 |
| WO | 2009132212 A2 | 10/2009 | |
| WO | 2011102725 A1 | 8/2011 | |
| WO | 2011126144 A1 | 10/2011 | |
| WO | 2012065602 A2 | 5/2012 | |
| WO | 2013011185 A1 | 1/2013 | |
| WO | WO-2013059813 A1 * | 4/2013 | A61B 50/20 |
| WO | 2014179698 A3 | 2/2015 | |
| WO | 2016094387 A3 | 6/2016 | |
| WO | 2020176818 A1 | 9/2020 | |
| WO | WO-2021108257 A1 * | 6/2021 | A61J 1/2096 |

* cited by examiner

DEVICE AND SYSTEM FOR INJECTING BIOLOGICAL TISSUE

CROSS-REFERENCE TO RELATED APPLICATIONS

N/A.

GOVERNMENT RIGHTS STATEMENT

N/A.

TECHNICAL FIELD

This disclosure relates generally to a device and method for aspirating tissue and delivering the tissue to a target delivery site.

BACKGROUND

Corneal transplants or grafts are the most common and successful transplantation procedures in medicine. In fact, more than 280,000 donor corneas are recovered every year and at least 180,000 corneal transplants are performed annually worldwide. According to a global survey that was conducted between 2012 and 2013, around 40% of the corneas were recovered in the United States.

The cornea is the clear, protective outer layer of the eye, and consists primarily of three layers, namely, the corneal epithelium (outer layer), the corneal stroma, and the corneal endothelium (inner layer). Each layer has different characteristics. For example, the corneal epithelium is a thin multicellular epithelial tissue layer of fast-growing and easily regenerated cells. The corneal stroma is a thick transparent middle layer that includes regularly arranged collagen fibers and keratocytes, which are the cells that help maintain the structure of the corneal stroma. The corneal stroma consists of approximately 200 layers of mainly type I and type V collagen fibers. Up to 90% of the corneal thickness is composed of stroma.

Finally, the corneal endothelium is a monolayer of mitochondria-rich cells. These cells are responsible for regulating fluid and solute transport between the aqueous humor and corneal stroma. Unlike the corneal epithelium, endothelial cells do not regenerate. Instead, they stretch to compensate for dead cells, which reduces the overall cell density of the endothelium, which affects fluid regulation. If endothelial cells can no longer maintain a proper fluid balance, stromal swelling due to excess fluids and subsequent loss of transparency will occur, which may cause corneal edema.

Fuchs' endothelial dystrophy and pseudophakic bullous keratopathy (PBK) are two of the most frequent indications for corneal transplantation. Until a few years ago, full thickness corneal transplantation was the only available treatment for endothelial layer replacement. However, although this procedure is able to restore corneal endothelial function, it has several drawbacks, such as high postoperative astigmatism, risk of tissue dehiscence and risk of infections and tissue rejection.

In the 1960s, a method of endothelial keratoplasty (EK) using an anterior approach via a laser-assisted in situ keratomileusis (LASIK) flap was described, and in 1999, a technique for posterior lamellar keratoplasty was developed. In a procedure called posterior lamellar keratoplasty (PLK), the posterior lamella, Descemet's membrane, and endothelium was dissected through a 9-mm sclerocorneal incision. A donor button consisting of posterior stroma, Descemet's membrane, and endothelium was then inserted and held in place by an air bubble while the patient lay supine.

In the 1990s, as the PLK procedure was further modified and a procedure called deep lamellar endothelial keratoplasty (DLEK) was developed. DLEK eliminated surface corneal sutures and incisions, leading to faster visual rehabilitation. However, DLEK requires the manual lamellar dissection of the deep corneal stroma from both donor and recipient, which is considered by surgeons to be difficult and laborious.

This consequently led to the development of Descemet's stripping endothelial keratoplasty (DSEK). DSEK has the advantages of being easier for the surgeon to perform and of providing a smoother interface on the recipient side for the visual axis. Preparation of the donor tissue in endothelial keratoplasty has also been made easier with the utilization of an automated microkeratome. The addition of this component to the surgical procedure has been popularized as Descemet's stripping automated endothelial keratoplasty (DSAEK).

Descemet's membrane endothelial keratoplasty (DMEK) is a partial-thickness cornea transplant procedure that involves a selective transplantation of a monolayer of donor endothelial cells and Descemet's membrane in the absence of a stromal tissue carrier. While the idea of DMEK was first introduced in 1998, the first successful report of DMEK did not occur until 2006.

In the DMEK technique, the donor corneoscleral rim is positioned with the endothelial side up. The scleral spur and Descemet's membrane are separated for 360 degrees, after which a superficial trephination of approximately 9 mm is made in the posterior stroma. The donor corneoscleral rim is submerged under Optisol or balanced saline solution (BSS) to decrease the surface tension and lower the risk of a potential Descemet's membrane tear. The endothelium is stripped from the posterior donor stroma with nontoothed forceps, creating a circular sheet of Descemet's membrane with an endothelial monolayer of cells. Owing to the elastic properties of the Descemet's membrane, a "Descemet's roll" forms spontaneously after the circular layer of endothelium/Descemet's membrane is removed from the donor posterior stroma, with the endothelium on the outside of the roll. The roll of tissue is stained with 0.06% trypan blue. The tissue is next placed in a tissue injector. Next, a scleral or corneal incision is made. With a reverse Sinskey hook, a circular portion of Descemet's membrane is scored and stripped from the recipient posterior stroma, completing a 9.0-mm diameter "descemetorhexis." The stripped Descemet's membrane and endothelium are removed from the eye. Using the injector, the donor tissue roll is inserted into the anterior chamber and the graft is oriented endothelial side down by indirect manipulation of the tissue with air and/or fluid. While maintaining the anterior chamber with fluid and air, the graft is gently spread out over the iris. Then, an air bubble is injected underneath the donor Descemet's membrane to position the tissue onto the recipient posterior stroma. The anterior chamber is completely filled with air for 30 to 60 minutes followed by an air-liquid exchange to pressurize the eye.

Loading of the tissue into the injector and inserting the tissue into the anterior chamber are two of the most important steps in the DMEK procedure. Loading of the tissue requires controlled vacuum to draw the tissue towards the injector. Some injectors require the tissue to be loaded through the injection end, which is narrow and makes the aspiration more difficult and traumatic. For this reason, new injectors allow the tissue to be loaded through the connection part of the injector, which has a larger diameter and makes the aspiration easier and less traumatic for the tissue. However, these types of injectors require extra tubing to aspirate the tissue, as the syringe cannot be adapted to the connection part of the injector. Additionally, aspiration of the tissue requires vacuum, which sometimes is difficult to control and causes the tissue to be aspirated too rapidly or to slowly. This can cause the tissue to hit the walls of the injector, potentially causing endothelial cell loss.

On the other hand, insertion of the tissue into the anterior chamber is performed by pressing the plunger of a syringe preloaded with BSS. Unfortunately, pressure cannot be accurately controlled and the tissue is often injected too rapidly into the anterior chamber and hits the anterior chamber angle, which can cause endothelial cell loss. Additionally, to minimize the induced astigmatism caused by the incision and to improve chamber stability, new injectors have a smaller diameter that can go through small incisions of approximately 2.5 mm. However, this smaller injector diameter causes more friction against the tissue and may also cause endothelial cell loss during tissue insertion.

Additionally, injection devices and systems that provide more controlled injection of tissue, more precise tissue placement, and better storage of collected tissue are needed not only for the DMEK procedure, but also for many other types of medical procedures, including but not limited to intraocular lens insertion, pupil expansion device insertion, DSEK, ultrathin DSEK (UT-DSEK), nanothin DSEK (NT-DSEK), or bioengineered membrane endothelial keratoplasty.

SUMMARY

Some embodiments advantageously provide a device, system, and method for aspirating graft tissue and delivering the graft tissue to a target delivery site. In one non-limiting example, the device and method may be used to deliver graft tissue to a location within an anterior chamber of an eye when performing Descemet's membrane endothelial keratoplasty. In some embodiments, the techniques described herein relate to an injector kit, the injector kit including an injector including a body and a plunger movably positionable within the body, the body including: a first end having a first opening; a second end opposite the first end, the second end having a second opening and an end wall at least partially defining the second opening; a chamber extending from the first end to the second end, the chamber being in fluid communication with the first opening and the second opening, the chamber being at least partially defined by an inner surface of the body, at least a portion of the inner surface defining a threading; a stalk extending from the end wall; and a connection extension extending from the second end of the body, the connection extension including a first end extending from the second end of the body, an opening, and a chamber therebetween, the stalk being located within the chamber of the connection extension.

In some aspects of the embodiment, the injector kit further includes a plunger, the plunger including: a shaft having a first portion and a second portion opposite the first portion, the second portion having a free end; and a knob coupled to the first portion, an outer surface of at least a portion of the first portion defining a protrusion, the protrusion being located a distance from the knob and being sized and configured to rotatably engage with the threading of the body, the plunger being rotatably advanceable and linearly advanceable within the body and rotatably retractable and linearly retractable within the body.

In some aspects of the embodiment, the stalk includes: a first end meeting the end wall; a second end opposite the first end, the second end defining an opening; and a lumen, the lumen being in fluid communication with the second opening of the body and the second opening of the stalk, the stalk and the connection extension being coaxial.

In some aspects of the embodiment, the body has a first longitudinal axis and the connection extension has a second longitudinal axis that is different than the first longitudinal axis, the second longitudinal axis being oriented at an angle from the first longitudinal axis. In some aspects of the embodiment, the techniques described herein relate to a injector kit, wherein the angle is less than approximately 90°. In some aspects of the embodiment, the techniques described herein relate to a injector kit, wherein the second longitudinal axis is oriented at an angle from the first longitudinal axis, the angle being between approximately 22.5° and approximately 67.5°.

In some aspects, the injector kit further includes a tissue cartridge including: a first portion defining a first opening and having a first outer diameter, the first opening having a first diameter; a second portion opposite the first portion and defining a second opening, the second portion having a second outer diameter that is less than the first outer diameter of the first portion and the second opening having a second diameter that is less than the first diameter of the first opening; and a chamber, the chamber being in fluid communication with the first opening of the tissue cartridge and the second opening of the tissue cartridge.

In some aspects of the embodiment, the injector kit further includes a cartridge coupling element, the cartridge coupling element including: a first portion including a friction fit element, the friction fit element having an opening with a diameter; and a second portion including a collar, the collar being configured to be coupled to the tissue cartridge.

In some aspects of the embodiment, the cartridge coupling element is configured to be coupled to the tissue cartridge by a luer lock.

In some aspects of the embodiment, the friction fit element is sized and configured to be at least partially received within and to fit in close tolerance within the chamber of the connection extension; the stalk has an outer diameter that is slightly smaller than the diameter of the opening of the friction fit element, such that the stalk is removably insertable within the opening of the stalk and securable therein by friction fit when the friction fit element is at least partially received within the chamber of the connection extension; and the opening of the stalk has an inner diameter that is slightly larger than the outer diameter of the second portion of the tissue cartridge, such that the second portion of the tissue cartridge is removably insertable within the opening of the stalk and securable therein by friction fit.

In some aspects of the embodiment, the injector kit further includes a container, the container including: a base, the base having an upper face and a well, the well being configured to contain a volume of liquid, the well including a first portion and at least one second portion extending away from the first portion, a first end of the first portion being sized and configured to retain the tissue cartridge and a second end of the first portion having a ramp, the ramp being sloped downward toward the first end of the first portion; and a lid that is removably couplable to the base. In some aspects of the embodiment, the ramp is configured to guide the body of the injector toward the tissue cartridge when the tissue cartridge is retained within the first end of the first portion.

In some aspects of the embodiment, the upper face includes: a first fluid barrier surrounding the well; and a second fluid barrier surrounding and being a distance from the first fluid barrier.

In some aspects of the embodiment, the first end of the first portion of the well includes at least one cartridge retainment element configured to hold the tissue cartridge in place.

In one embodiment, the techniques described herein relate to a container for a tissue cartridge, the container including: a base, the base including: an upper face; and a well extending downward from the upper face, the well including a first end configured to retain a tissue cartridge and a second end with a ramp that slopes downward toward the first end, the upper face including a first fluid barrier surrounding the well and a second fluid barrier surrounding the first fluid barrier; and a lid, the lid being removably couplable to the base.

In some aspects of the embodiment, the first end and the second end are in a first portion of the well, the well further including at least one second portion extending away from the first portion, each of the at least one second portion being sized and configured to accept at least a portion of a human finger.

In some aspects of the embodiment, the well and the first fluid barrier are configured to contain a first volume of solution; and the first fluid barrier and the second fluid barrier are configured to contain a second volume of solution, the second volume of solution being less than the first volume of solution.

In some aspects of the embodiment, the first volume is approximately 20 mL.

In one embodiment, the techniques described herein relate to a method of coupling an injector to a tissue cartridge, the method including: retaining the tissue cartridge within a well of a container, the well including a first end including at least one cartridge retainment element for holding the cartridge in place and a second end including a ramp that slopes downward toward the first end; inserting a connection end of an injector into the well; sliding the connection end of the injector down the ramp toward the tissue cartridge; engaging the tissue cartridge with the connection end of the injector; and lifting the injector, with cartridge attached, out of the well.

In some aspects of the embodiment, the cartridge is coupled to a cartridge coupling element, the step of engaging the tissue cartridge with the connection end of the injector including inserting at least a portion of a stalk of the connection end of the injector into the cartridge coupling element.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
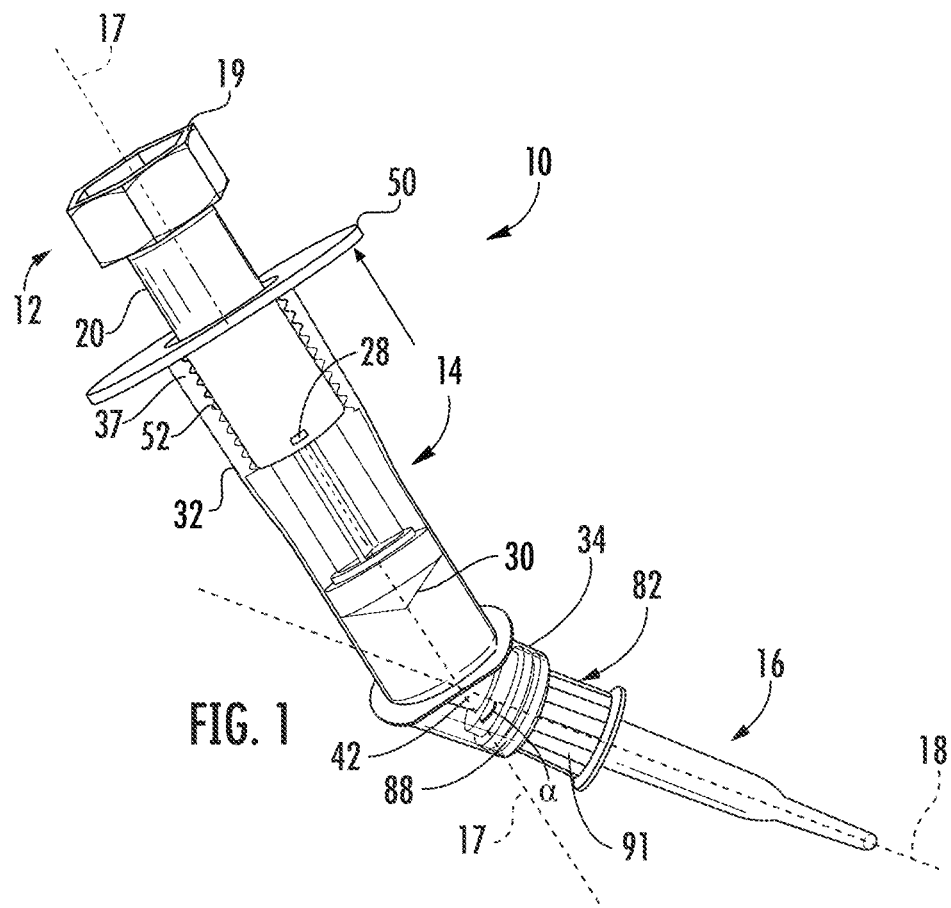
FIG. 1 shows an exemplary embodiment of an injector having a plunger and a tissue cartridge in accordance with the present disclosure, the plunger being in a first position and the tissue cartridge being in an injection configuration.

Before describing in detail exemplary embodiments, it is noted that the embodiments reside primarily in combinations of apparatus components and steps related to aspirating graft tissue into an injector and delivering (injector or ejecting) the graft tissue to a delivery location. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof. Further, as used herein, "and/or" means "and" or "or". For example, "A and/or B" means "A, B, or both A and B" and "A, B, C, and/or D" means "A, B, C, D, or a combination thereof" and said "A, B, C, D, or a combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The terms "corneal transplant" and "corneal graft" are used interchangeably herein to refer to a medical procedure, and the term "corneal graft tissue" is used herein to refer to the tissue used for the medical procedure of corneal transplant or corneal graft.

Figure 2:
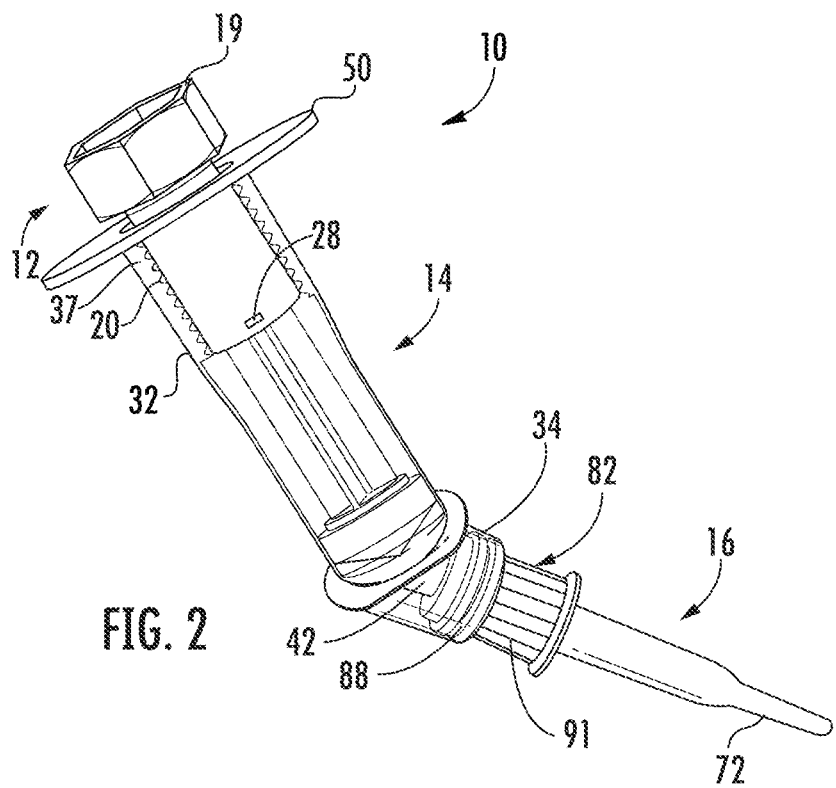
FIG. 2 shows the injector of FIG. 1, the plunger being in a second position and the tissue cartridge being in the injection configuration in accordance with the present disclosure.
Figure 3:
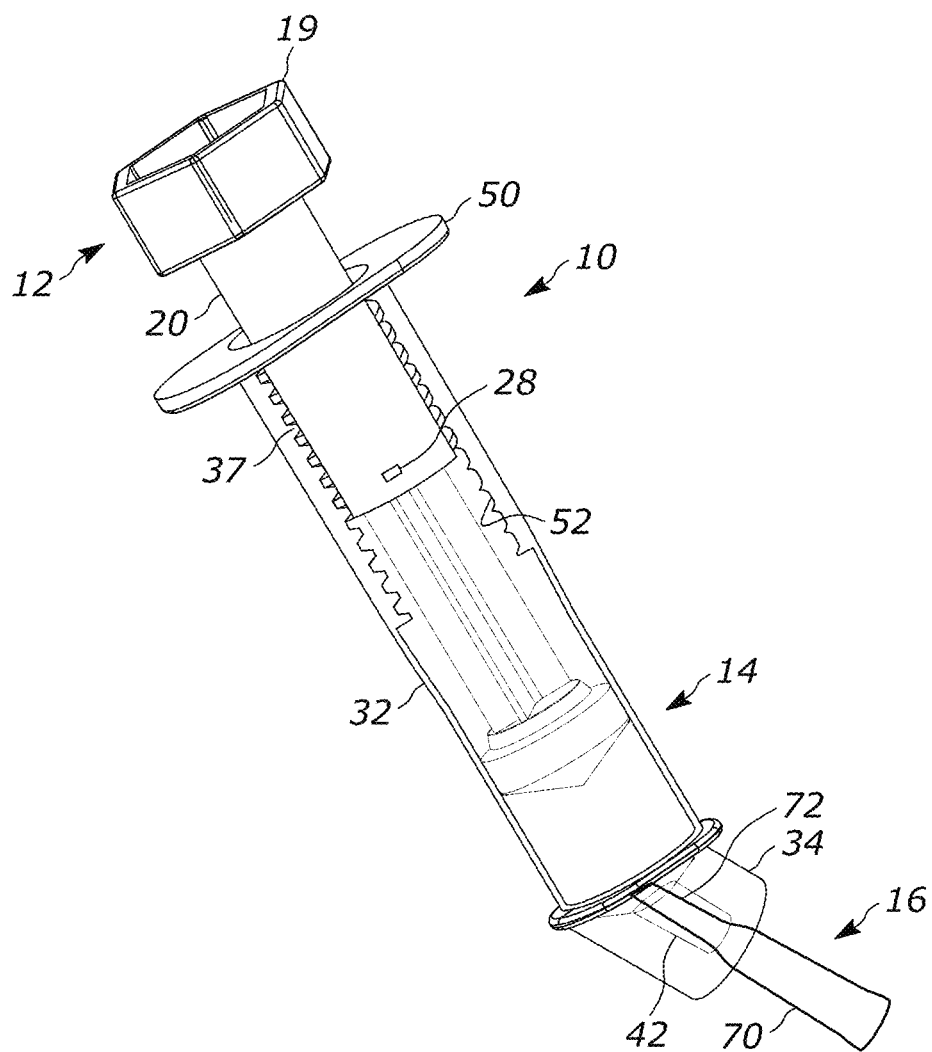
FIG. 3 shows the injector of FIG. 1, the tissue cartridge being in an aspiration configuration in accordance with the present disclosure.

Referring now to the figures in which like reference designators are used for like elements, a graft tissue injector 10 (also referred to herein as an injector 10) is shown in FIGS. 1-3. FIGS. 1 and 2 show the injector 10 in an injection configuration (or second configuration, when the injector 10 is in use) and FIG. 3 shows the injector 10 in an aspiration configuration (or first configuration, when the injector 10 is in use). The injector 10 is configured for use in a medical procedure. In one non-limiting example, the injector 10 is configured for use in a Descemet's membrane endothelial keratoplasty (DMEK), but it will be understood that the injector 10 and/or other components of the associated system may be used for other medical procedures. In one embodiment, the injector 10 is configured to aspirate a rolled piece of donor corneal tissue (referred to herein as "graft tissue"), including at least a portion of an endothelium and a Descemet's membrane, into the injector 10 for subsequent injection into an anterior chamber of a patient's eye (the aqueous humor-filled space inside the eye between the iris and the corneal endothelium).

Generally referring to the figures, in some embodiments the injector 10 generally includes a plunger 12, a cylinder 14, and includes or is configured to include a tissue cartridge 16 (also referred to herein as a "cartridge 16" for simplicity) that is removably couplable to the cylinder 14. When the injector 10 is assembled, the injector 10 has a bent shape, with a first portion having a first longitudinal axis 17 and a second portion having a second longitudinal axis 18 that is different than the first longitudinal axis 17. In one embodiment, the first portion includes the plunger 12 and at least a portion of the cylinder 14 and the second portion includes at least a portion of the cylinder 14 and the cartridge 16 (for example, as shown in FIG. 1). To use the injector 10, the user engages with the plunger 12 to retract the plunger 12 a distance within the cylinder 14, thereby aspirating a graft tissue into the injector 10. Conversely, to inject the graft tissue from the injector 10 into or at a delivery site, the user engages with the plunger 12 to advance the plunger 12 in an opposite direction a distance within the cylinder 14, thereby ejecting the graft tissue from the injector 10. Additionally, as is discussed in greater detail below, in one embodiment the cartridge 16 is in a first position when graft tissue is aspirated into the graft tissue injector 10 (for example, as shown in FIG. 3) and the cartridge 16 is in a second position when graft tissue is injected from the graft tissue injector 10 (for example, as shown in FIG. 2).

Referring now generally to FIGS. 1-5, the injector 10 generally includes a threaded plunger 12 and a threaded cylinder 14. In one exemplary method of use, to aspirate graft tissue into the injector 10, the plunger 12 is longitudinally retracted without required rotation and, optionally, then rotated in a first direction (for example, counterclockwise) to draw the plunger 12 within the cylinder 14 and away from the cartridge 16 (for example, in the direction indicated by the arrow in FIG. 1). Conversely, to inject the graft tissue from the injector 10 into or at a delivery site, the plunger 12 is rotated in a second direction opposite the first direction (for example, clockwise) and, optionally, then longitudinally advanced without required rotation to move the plunger 12 within the cylinder 14 toward the cartridge 16 (for example, in the direction indicated by the arrow in FIG. 2). Movement of the plunger 12 within the cylinder 14 is described in greater detail below.

Figure 4:
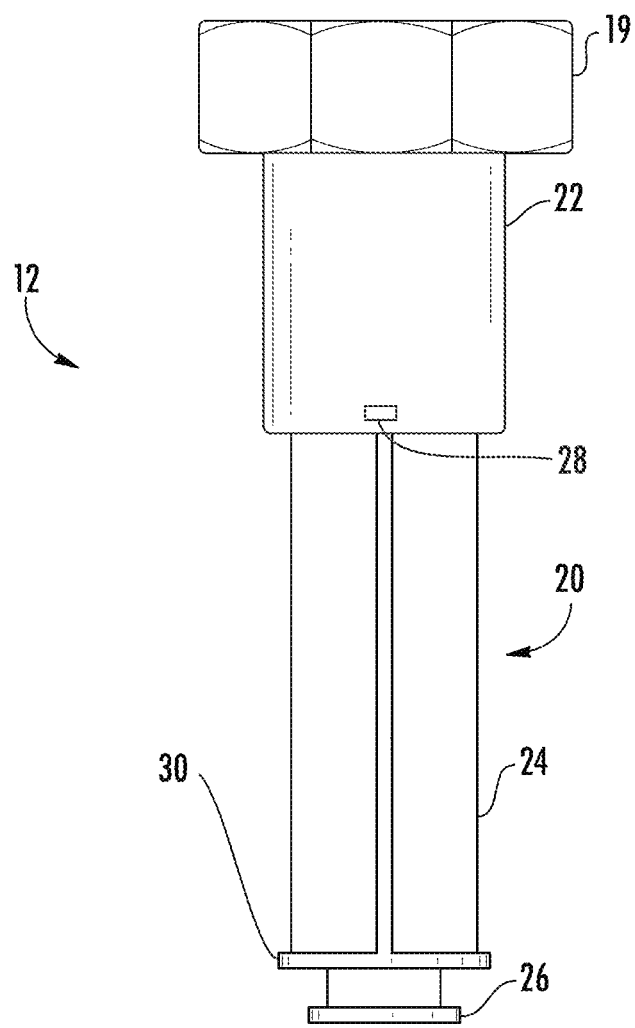
FIG. 4 shows an exemplary embodiment of the plunger for an injector, for example, an injector of FIG. 1, in accordance with the present disclosure.

Referring now to FIG. 4, the plunger 12 is shown in greater detail. In one embodiment, the plunger 12 has an elongated shape and generally includes a knob 19 and a shaft 20. In one embodiment, the knob 19 is polygonal in cross section, but it will be understood that the knob 19 may have any suitable size, shape, and/or configuration that is easily graspable by the user and that the knob 19 is not limited to the embodiment shown. In one embodiment, the shaft 20 has an elongated shape and includes a first portion 22 coupled to, fused with, or extending from the knob 19 and a second portion 24 opposite the first portion 22, the second portion 24 including a free end 26. At least a portion of the shaft 20 is threaded. In one embodiment, an outer surface of at least a portion of the first portion 22 of the shaft 20 includes a protrusion 28, such as a tab, ridge, lip, flange, or other suitable structure, that is located a distance from the knob 19 and between the first portion 22 and the second portion 24 of the shaft 20. As discussed below, the protrusion 28 is sized and configured to engage with an inner surface of the cylinder 14. However, in other embodiments the outer surface of at least a portion of the first portion 22 of the shaft 20 includes threading (not shown) instead of the protrusion. Thus, in one embodiment, the first portion 22 includes a threaded portion and an unthreaded portion between the knob 19 and the threaded portion. In other embodiments, the threading is not continuous, and includes one or more interruptions or non-threaded portions. The threading may be continuous threading that extends around the shaft 20 at least once, or at least 360°, without break or interruption. Optionally, the shaft 20 may also include one or more areas, such as at or proximate the free end 26, that include a material such as rubber or a similar material, or simply protrusions from and formed of the same material as the shaft 20, that enhances contact between the shaft 20 and an inner surface 37 of the cylinder 14. This may prevent leaks and thereby help force liquid, and the graft tissue, from the injector 10 when the plunger 12 is advanced within the cylinder 14. Further, in some embodiments the free end 26 includes or is coupled to an end piece of material, which may be composed of, for example, rubber or a similar material. In some embodiments, the free end 26 is co-molded or formed with an integrated stopper that is composed of the same or different material than the shaft 20. In some embodiments, the stopper is an end piece of material that is affixed, adhered, or otherwise coupled to the free end 26.

Figure 5:
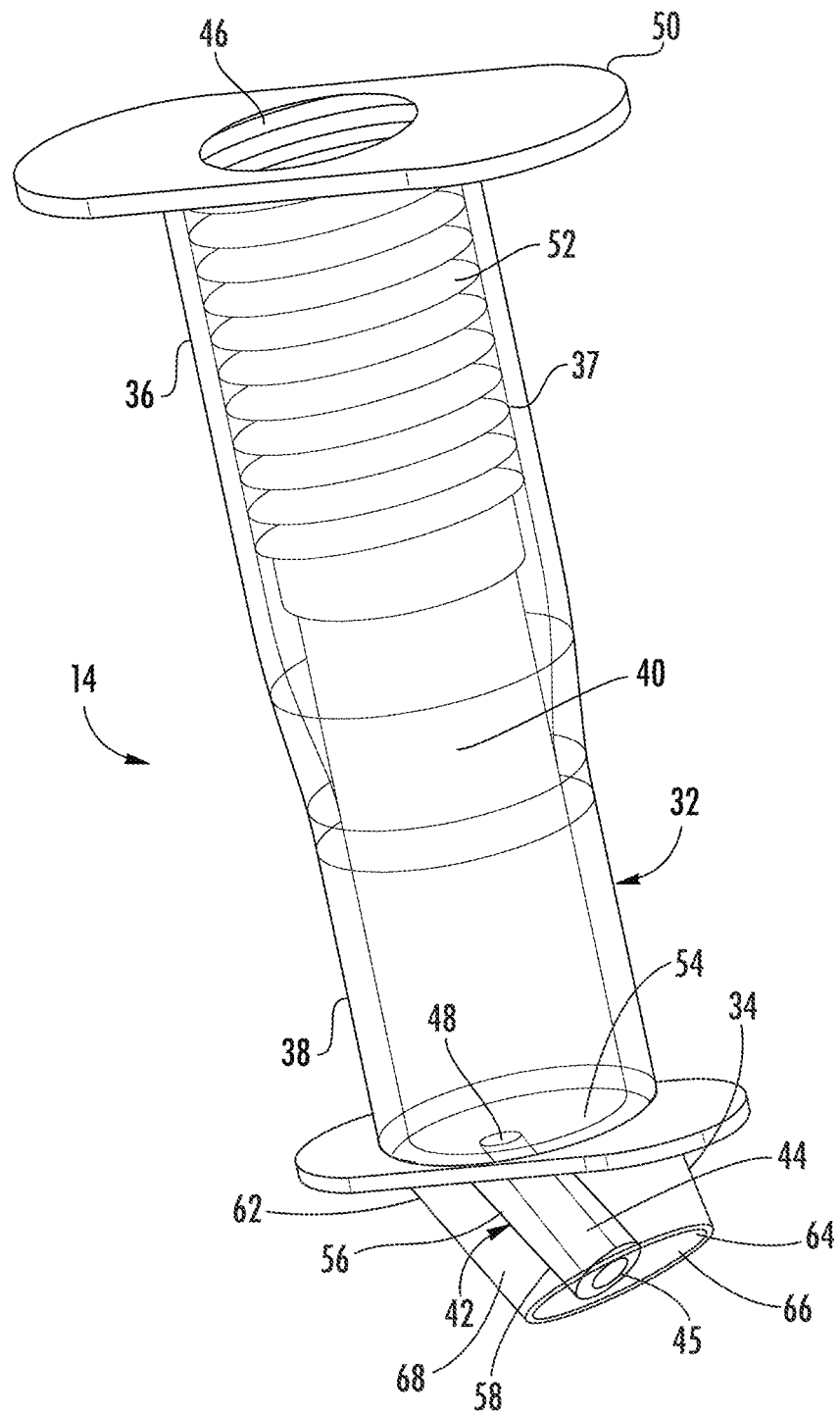
FIG. 5 shows an exemplary embodiment of a cylinder of the injector of FIG. 1 in accordance with the present disclosure.

Referring now to FIG. 5, the cylinder 14 is shown in greater detail. In one embodiment, the cylinder 14 includes an elongate body 32 that is tubular or at least substantially tubular and a connection extension 34 that is coupled to or extends from one end of the body 32 at an angle from the first longitudinal axis 17. For example, the connection extension 34 and the cartridge 16 may extend along the same second longitudinal axis 18 when the cartridge 16 is attached to the body 32. In one embodiment, the body 32 generally includes a first end 36, a second end 38 opposite the first end 36, and a chamber 40 therebetween. The chamber 40 is at least partially defined by the inner surface 37 of the body 32. In one embodiment, the body 32 further includes a stalk 42 that extends from (and may be coupled to or integrated with) the second end 38 of the body 32 at an angle, along the same longitudinal axis 18 as the connection extension 34. Likewise, the connection extension 34 extends from (and may be coupled to or integrated with) the second end 38 and forms a hood that encircles the stalk 42. Put another way, the stalk 42 is located within and coaxial with the connection extension 34. The stalk 42 includes a lumen 44 that extends therethrough and a distal opening 45 that is in fluid communication with the lumen 44.

Continuing to refer to FIG. 5, in one embodiment the first end 36 of the body 32 defines a first opening 46 and the second end 38 of the body 32 defines a second opening 48, and the first opening 46 has a larger inner diameter than the second opening 48. The first opening 46 and the second opening 48 are each in fluid communication with the chamber 40. In some embodiments, the body 32 has a continuous, or at least substantially continuous, outer diameter and/or inner diameter along its entire length. In one non-limiting example, the chamber 40 has a continuous, or at least substantially continuous, diameter (that is, the body 32 has a continuous, or at least substantially continuous, inner diameter) along its length that is the same as, or at least substantially the same as, the inner diameter of the first opening 46. In other embodiments, the body 32 has a varying outer and/or inner diameter. In some embodiments, the cylinder 14 includes a finger grip or flange 50 extending from the first end 36 of the body and extending at least partially around the first opening 46.

Continuing to refer to FIG. 5, in one embodiment the first opening 46 and at least a portion of the chamber 40 (for example, a portion of the chamber 40 that is proximate the first end 36 of the body 32) is sized and configured to receive at least a portion of the shaft 20 of the plunger 12 in close tolerance, such that fluid does not escape the injector 10 when the shaft 20 is rotated or advanced within the body 32. Additionally, at least a portion of the body 32 includes threading 52 within the chamber 40, on the inner surface 37 of the body 32. In one embodiment, the body 32 includes threading 52 within the chamber 40 on the inner surface 37 extending from the first opening 46 toward the second opening 48 and over a distance. The number of times the threading 52 passes around 360° of the inner surface of the body 32 depends on the characteristics of the threading 52, such as pitch, size, thread angle, and the like, and/or the size and configuration of the protrusion 28. Further, the distance along the longitudinal axis 17 over which the threading 52 extends may be more or less than that shown in the Figures. That is, the inner surface 37 of the body 32 may include a greater or smaller area of threading than shown. The amount of threading 52 may depend, for example, on the type of medical procedure for which the injector 10 will be used, the distance over which the plunger 12 should be rotated (to controllably aspirate and/or inject graft tissue or other material), the distance over which the plunger 12 should be freely and linearly movable along the longitudinal axis 17 without requiring rotation, and/or other considerations. The protrusion 28 is sized and configured to rotatably engage with the threading 52 in the chamber 40. Put another way, the protrusion 28 of the shaft 20 is complementary to and engageable with the threading 52 in the chamber 40. Thus, the shaft 20 of the plunger 12 may be screwed into, and rotatably movable within (that is, advanceable and retractable along the first longitudinal axis 17 of the cylinder 14), at least a portion of the chamber 40 of the body 32. In one embodiment, the protrusion 28 is elongate and generally extends across the longitudinal axis 17 of the cylinder 14, and has a size and dimension based on the pitch, thread angle, and/or other characteristics of the threading 52 that allows the protrusion 28 to move smoothly and securely within the threading 52. Thus, the protrusion 28 may define a discontinuous male screw thread and the inner surface 37 of the body 32 defines the root of the screw threads. In some embodiments, the shaft 20 includes more than one protrusion 28 and/or protrusion(s) having a size, shape, or configuration other than shown that is still mateably engageable with the threading 52.

Continuing to refer to FIG. 5, in one embodiment the connection extension 34 and the stalk 42 extend from the second end 38 of the body 32. In one embodiment, the second end 38 of the body 32 includes an end wall 54 that surrounds or defines the second opening 48 and the stalk 42 extends from the end wall 54 to define the second longitudinal axis 18 of the injector 10. In one embodiment, the stalk 42 generally has a tubular shape, with a first end 56, a second end 58 opposite the first end 56, and the lumen 44 extends therebetween. The second end 58 defines an opening 45 in fluid communication with the lumen 44. As shown in FIG. 5, in one embodiment the first end 56 of the stalk 42 is coupled to or meets the end wall 54 of the body 32 such that the second opening 48 of the body 32 (and, therefore, the chamber 40) is in fluid communication with the lumen 44 and the opening 45 of the stalk 42. In one embodiment, the connection extension 34 also includes a first end 62, a second end 64 opposite the first end 62, and an opening 66 at the second end 64. The connection extension 34 defines a chamber 68 within which the stalk 42 is located, and the stalk 42 does not extend out of the chamber 68 beyond the second end 64 of the connection extension 34. Thus, the connection extension 34 and the stalk 42 are coaxial, and the connection extension 34 has a larger maximum outer diameter than the stalk 42.

Continuing to refer to FIG. 5, in one embodiment the stalk 42 has an outer diameter that is less than at least the diameter of the end wall 54. Likewise, in one embodiment the lumen 44 of the stalk 42 has a diameter that is less than the diameter of the chamber 40 within at least a portion of the body 32 (that is, the stalk 42 has an inner diameter that is less than the inner diameter of at least a portion of the body 32). Further, as is shown in FIG. 5, the connection extension 34 and stalk 42 are canted relative to the body 32 and extend along a common longitudinal axis 18 that is different than the longitudinal axis 17 along with the body 32 extends. However, it will be understood that in other embodiments, the connection extension 34 and the stalk 42 may extend along different longitudinal axes. In one embodiment, the first and second longitudinal axes 17, 18 intersect at an angle $\alpha$ of less than approximately 90° (±5°). In one embodiment, the angle $\alpha$ is between approximately 22.5° and approximately 67.5° (±5°). Thus, the injector 10 may be referred to as having a bent configuration, and this configuration may facilitate handling during operation (for example, during both aspiration of the graft tissue and insertion of the graft tissue into the delivery site, such as the anterior chamber of the patient's eye). When the cartridge 16 is coupled to the stalk 42, the cartridge 16 lies along the same longitudinal axis as the stalk 42 (i.e. the second longitudinal axis 18). Likewise, although axes 17, 18 are not shown in FIGS. 3 and 5, it will be understood that the injector 10 has the same bent configuration regardless of how the cartridge 16 is coupled to the stalk 42 (or whether a cartridge 16 is coupled to the stalk 42).

Continuing to refer to FIG. 5, in one embodiment, the connection extension 34, stalk 42, and the body 32 are formed as a single, unitary piece. In another embodiment, the connection extension 34 and/or the stalk 42 is rigidly or flexibly coupled to the body 32. In one embodiment the body 32, the connection extension 34, and the stalk 42 are composed of the same material. For example, the entire cylinder 14 may be composed of a rigid material that is transparent and/or translucent, such as glass, plastic, or polymer. Thus, the connection extension 34 and stalk 42 may be rigidly connected to or extend from the second end 38 of the body 32 and, therefore, cartridge 16 may be at a fixed position relative to the body 32 when connected to the stalk 42. In another embodiment, the body 32 and the connection extension 34 and/or the stalk 42 are composed of different materials. In one non-limiting example, the body 32 may be composed of a rigid first material (that is either opaque or transparent and/or translucent), such as glass, plastic, or polymer, whereas the connection extension 34 and/or the stalk 42 may be composed of a second material (that is either opaque or transparent and/or translucent) that is more flexible than, or that has a durometer that is less than, the material from which the body 32 is composed. This may allow some flexibility in the second portion of the injector 10 when in use. Put another way, when connected to the stalk 42, the cartridge 16 may be at least somewhat movable relative to the body 32.

Figure 6:
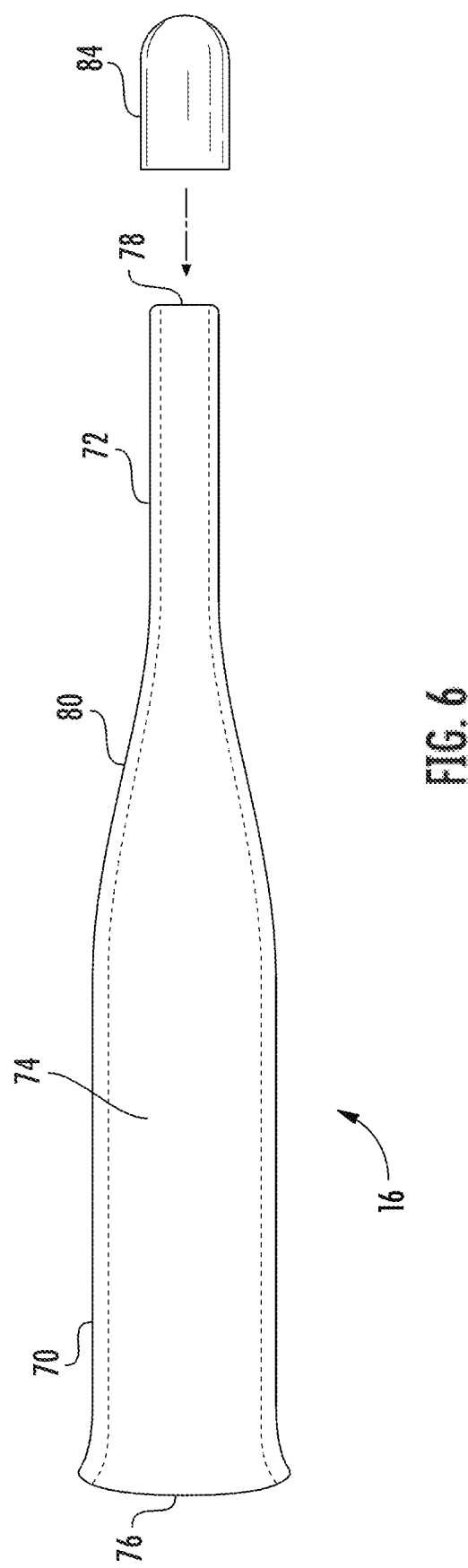
FIG. 6 shows an exemplary embodiment of a tissue cartridge for the injector in accordance with the present disclosure.
Figure 7:
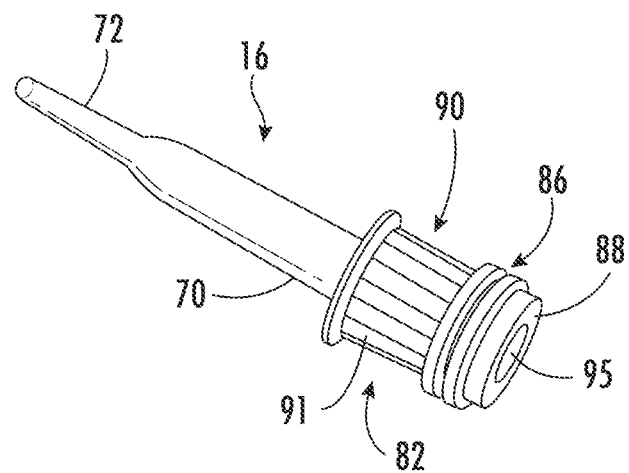
FIG. 7 shows the tissue cartridge of FIG. 6 with a cartridge coupling element, in accordance with the present disclosure.

Referring now to FIGS. 6 and 7, the cartridge 16 is shown in greater detail. In one embodiment, the cartridge 16 generally has an elongated shape (and, in some embodiments, has a flute shape, as shown in FIGS. 6 and 7) and includes a first portion 70, a second portion 72 opposite the first portion 70, and a chamber 74 therebetween. The chamber 74 is defined by an inner surface of the cartridge 16. In one embodiment, the first portion 70 defines a first opening 76 and the second portion 72 defines a second opening 78, and the first and second openings 76, 78 are each in fluid communication with the chamber 74. In one embodiment, the first opening 76 has a larger diameter than the second opening 78. Further, in one embodiment the first portion 70 has a first outer diameter and the second portion 72 has a second outer diameter that is less than the first outer diameter. The cartridge 16 may also include a transition portion 80 between the first and second portions 70, 72 that has varying outer diameters between the first and second outer diameters. Likewise, in one embodiment the chamber 74 within the first portion 70 has a first diameter and the second portion 72 has a second diameter that is less than the first diameter (that is, the first portion 70 of the cartridge 16 has an inner diameter that is greater than greater than the inner diameter of the second portion of the cartridge 16). The chamber 74 within the transition portion 80 may also have varying diameters between the diameters of the first and second portions 70, 72 (that is, the transition portion 80 of the cartridge 16 may have a varying inner diameter, or plurality of inner diameters, between the inner diameters of the first and second portions 70, 72). Put another way, in one embodiment the cartridge 16 and chamber 74 therein have a tapered shape, and the second portion of the cartridge 16 may be an elongate tube of reduced diameter that is sized and configured to be at least partially inserted through a corneoscleral incision for injection and placement of the graft tissue within the anterior chamber of the patient's eye. Further, in some embodiments, the second portion 72 of the cartridge 16 may have a blunt shape where the second portion 72 defines the second opening 78, and in other embodiments the second portion 72 has a beveled shape where the second portion 72 defines the second opening 78.

Continuing to refer to FIGS. 6 and 7, in one embodiment, the first portion 70 has a slight flute or flange shape surrounding the first opening 76. Further, in one embodiment the first opening 76 of the cartridge 16 and at least a portion of the chamber 74 (for example, the portion of the chamber 74 within the first portion 70 of the cartridge 16) is sized and configured to fit over at least the second end 58 of the stalk 42, such that the cartridge 16 may be secured to the cylinder 14 by a friction fit and the chamber 74 of the cartridge 16 is in fluid communication with the lumen 44 of the stalk 42 and, therefore, the chamber 40 of the body 32. Put another way, the inner diameter of the first opening 76 and at least a portion of the chamber 74 is slightly larger than the outer diameter of at least the second end 58 of the stalk 42 such that the cartridge 16 may be secured coupled to and removed from the stalk 42 by hand. Alternatively, as shown in FIG. 7 and discussed in greater detail below, the cartridge 16 may be coupled to a cartridge coupling element 82, and the cartridge coupling element 82 may be friction fit over at least the second end 58 of the stalk 42.

Continuing to refer to FIGS. 6 and 7, in one embodiment the outer diameter of the second portion 72 of the cartridge 16 is sized and configured to fit within the opening 45 of the stalk 42, such that the cartridge 16 may be secured to the cylinder 14 by a friction fit and the chamber 74 of the cartridge 16 is in fluid communication with the lumen 44 of the stalk 42 and, therefore, the chamber 40 of the body 32. Put another way, the inner diameter of the opening 45 is slightly larger than the outer diameter of second portion 72 of the cartridge 16. As is described in greater detail below, in one embodiment the second portion 72 of the cartridge 16 is engaged with the stalk 42 when aspirating fluid and graft tissue (as shown in FIG. 3), and the first portion 70 of the cartridge 16 is engaged with the stalk 42 when injecting fluid and graft tissue (as shown in FIGS. 1 and 2). Additionally, an inner and/or outer surface of the stalk 42 and an inner and/or outer surface of the cartridge 16 may optionally be matably threaded so the cartridge 16 may be screwed onto or into the stalk 42. Further, in some embodiments, the injector 10 further includes a cap 84 that is removably coupled or couplable to the second portion 72 of the cartridge 16 to prevent graft tissue from escaping the chamber 74 through the second opening 78 once the injector 10 has been used to aspirate graft tissue and/or for pre-loaded cartridges 16A, as discussed in greater detail below.

Continuing to refer to FIGS. 6 and 7, in one embodiment the cartridge 16 is composed of a rigid material that is transparent and/or translucent, such as glass, plastic, or polymer. For example, in one embodiment the cartridge 16 is composed of a clear polymer. This allows the cartridge 16 to have the same inner diameter(s), but smaller outer diameter(s), than commercially known cartridges composed of glass because certain polymers are more flexible and resistant to breakage than glass. Additionally, at least the portion of the second portion 72 surrounding the second opening 78 may be rounded or blunted to create an atraumatic tip. Alternatively, the portion of the second portion 72 surrounding the second opening 78 may be beveled or include a bevel, which may facilitate insertion of the cartridge into the eye. Thus, the cartridge 16 of the present disclosure may be not only less traumatic when used to inject a tissue graft because of its reduced outer diameter(s) (at least the outer diameter of the second portion 72) and/or rounded tip, which allows for a smaller incision, but also more break-resistant than cartridges 16 composed of glass. The diameter of the second opening 78 and/or the diameter of the second end 72 may be chosen to suit a particular medical procedure. For example, a cartridge 16 for use in a DSEK procedure may require a larger opening 78 than a cartridge 16 for use in a DMEK procedure, because the graft tissue is thicker. Further, in one embodiment at least a portion of the cartridge 16 is coated with at least one layer of a lubricious material that lowers the coefficient of friction of that portion of the cartridge 16, such as polytetrafluoroethylene (PTFE), a nano-ceramic, or the like. In one embodiment, the lubricious material has a coefficient of friction of between approximately 0.1 and approximately 0.5 (±0.1). For example, a nano-ceramic coating that has a coefficient of friction that is at least 50% less than glass may be used on the inner surface and/or the outer surface of the cartridge 16, which reduces the likelihood of damage of the tissue graft and the patient's tissue during insertion. In one embodiment, both the inner surface (within the chamber 74) and the outer surface of the second portion 72 of the cartridge 16 may be coated with at least one layer of a lubricous material or combination of lubricous materials.

Figure 8:
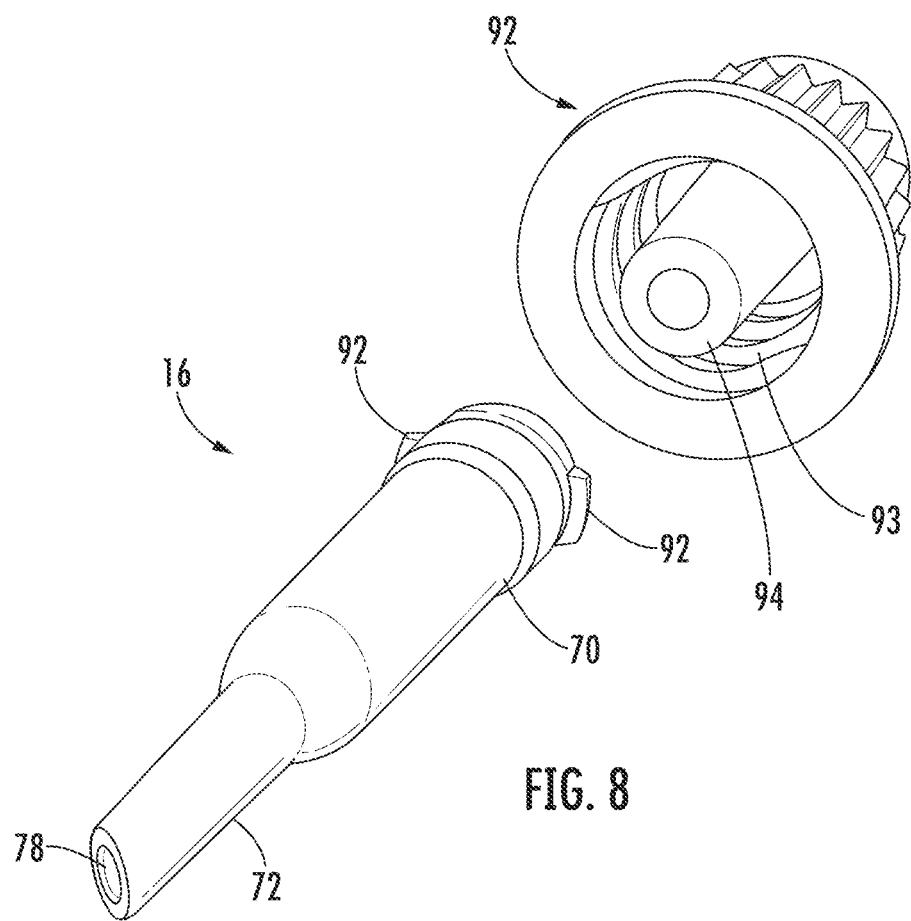
FIG. 8 shows an exemplary embodiment of a retainment element for use with an injector in accordance with the present disclosure.

Referring now to FIG. 7 and with reference to FIG. 8, in one embodiment the cartridge 16 is coupled to a cartridge coupling element 82 that facilitates attachment of the cartridge 16 to the body 32 and positioning of the cartridge 16 (and, therefore, the graft tissue or other contents within the cartridge 16) during use. In one embodiment, the cartridge coupling element 82 includes a first portion 86 with friction fit element 88 and a second portion 90 that defines a collar 91. In one embodiment, the cartridge 16 and the cartridge coupling element 82 are removably connectable to each other by a luer lock, luer slip, or other secure and leak-proof connection, thus preventing leaks or fluid escape between the cartridge 16 and the cartridge coupling element 82. For example, an outer surface of the second portion 72 of the cartridge 16 may include at least one first luer lock component 92 and an inner surface of the cartridge coupling element 82 (for example, the collar 91) may include at least one second luer lock component 93 that is matably engageable with the first luer lock component 92. In one embodiment, the cartridge 16 includes at least one tab, on the first portion 70 at a location that is at or proximate the first opening 76, as the first luer lock component 92 and the inner surface of the collar 91 includes luer lock threading as the second luer lock component 93 that is sized and configured to receive the at least one tab. For example, FIG. 8 shows the cartridge 16 and cartridge coupling element 82 separated, but aligned for connection to illustrate the luer lock components. In one embodiment, the cartridge coupling element 82 includes a male portion or stalk 94 that is sized and configured to be at least partially inserted into the first opening 76 of the cartridge 16, such that at least a portion of the cartridge 16 is sandwiched between the stalk 94 and the inside of the collar 91. Further, in one embodiment the stalk 94 includes an opening that, when the cartridge coupling element 82 is coupled to the cartridge 16, is in fluid communication with the chamber 74 of the cartridge 16. Alternatively, the cartridge coupling element 82 and the cartridge 16 may include complementary threading that allows the cartridge coupling element 82 to be screwed onto the cartridge 16. However, other means of secure connection may be used, such as threading, clips, clasps, and the like.

Continuing to refer to FIG. 7, the friction fit element 88 includes an opening 95 that is in fluid communication with the chamber 74 of the cartridge 16 and the opening of the stalk 94 of the collar 91, and the opening 95 is sized and configured to engage with (for example, fit over or accept therein) at least a portion of the second end 58 of the stalk 42 within the connection extension 34. Additionally, the friction fit element 88 is sized and configured such that, when the second end 58 of the stalk 42 is inserted within the opening 95, the friction fit element 88 fits within, and is in contact with the inner surfaces of, the connection extension 34 and the chamber 74 of the cartridge 16 is in fluid communication with the chamber 40 of the body 32. In this manner, the cartridge 16 may be removably coupled to the stalk 42 within the connection extension 34 by friction fit of the friction fit element 88 of the cartridge coupling element 82. In one embodiment, the friction fit element 88 is a generally tubular body composed of a resiliently compressible and/or deformable material, such as natural or synthetic rubber or rubberized material, that provides a suitable coefficient of friction when coupled to the stalk 42 within the connection extension 34. In one embodiment, the friction fit element 88 is sized and configured to fit in close tolerance within the chamber 68 of the connection extension 34 when the stalk 42 is at least partially received within the opening 95. Further, the opening 95 leads into a lumen that extends through the first portion 86 and the second portion 90, and is configured to be in fluid communication with the chamber 74 of the cartridge 16 when the cartridge coupling element 82 is coupled to the cartridge 16. In one embodiment, the collar 91 is composed of a rigid or semi-rigid material, such as glass, plastic, and/or polymer. The friction fit element 88 may be affixed to or overlayed onto the collar 91 by chemical welding, adhesive bonding, or other suitable method.

Continuing to refer to FIG. 7, when the cartridge 16 is securely connected to the cartridge coupling element 82 and in use or ready for use, the cartridge 16 is locked in position relative to the cartridge coupling element 82 (that is, the cartridge 16 is not rotatable relative to the cartridge coupling element 82. Conversely, in one embodiment, the cartridge coupling element 82 permits the cartridge 16 to be rotated around its axis 18 relative to the stalk 42. For example, when the cartridge is connected to the cylinder 14, the friction fit element 88 may be rotated around the stalk 42 within the connection extension 34 without uncoupling the cartridge 16 from the cylinder 14, which allows the cartridge 16 to be rotated about its axis 18. This may be useful during an injection procedure, such as a tissue graft transplant, to reposition the tissue or other material within the cartridge 16 and ensure it is in the best position possible for implantation.

Referring again generally to FIGS. 1-5, in one exemplary method of use, the user draws the plunger 12 through the chamber 40 in a direction away from the cartridge 16 to aspirate graft tissue (or other material) into the cartridge 16. Depending on the starting location of the plunger 12 within the chamber 40, the user may freely and more quickly retract the plunger 12 within the chamber 40 until the protrusion 28 on the shaft 20 becomes engaged with the threading 52 within the chamber 40. At this point, the user may then rotate the plunger 12 in a first direction (for example, in a counter-clockwise direction) to slowly retract the plunger 12 further.

Further, in one exemplary method of use, the user rotates the plunger 12 in a second direction (for example, clockwise), with the protrusion 28 engaged with the threading 52, to advance the plunger 12. When the plunger 12 is rotated, advancement of the plunger 12 within the chamber 40 is slower, which provides greater control over injection or delivery of the graft tissue to the delivery site. Thus, a user will be physically prevented from quickly injecting the graft tissue, and instead will gently inject the graft tissue at a slower rate. This may prevent injury to the patient, loss of the graft tissue, or other inadvertent errors. In some embodiments, the graft tissue has been injected from the injector 10 by the time the protrusion 28 disengages with the threading 52. However, the user may further advance the plunger 12. If the user rotates the plunger 12 enough times to disengage the protrusion 28 from the threading 52 (that is, the protrusion 28 is advanced toward the cartridge 16 and beyond the threading 52), the user may then freely and longitudinally advance the plunger 12 through the chamber 40 without the need for rotation. For example, this may allow for the rapid ejection of all remaining fluid from the injector 10.

It will be further appreciated that more than one injector 10 may be used during a given procedure or series of procedures. For example, a user may use both a first injector 10 to aspirate graft tissue into the cartridge 16 and a second injector 10 (for example, when the collected graft tissue is contained within the cartridge 16 for later use). In one non-limiting example, the user may aspirate the graft tissue using the first injector 10, remove the cartridge 16 from the first injector 10 and then secure the cap 84 to the cartridge 16 to obstruct or cover the second opening 78, and then connect the first portion 70 of the cartridge 16 to the stalk 42 of a second injector 10. Once the user is ready to begin the graft tissue delivery procedure, the user may the remove the cap 84 from the cartridge 16. However, it will be understood that the user may use a single injector 10 or any combination of multiple injectors 10 and/or combinations of cylinder(s) 14 and plunger(s) 12, depending on the type of procedure, time between aspiration and delivery of graft tissue, user preference, or the like.

Figure 9:
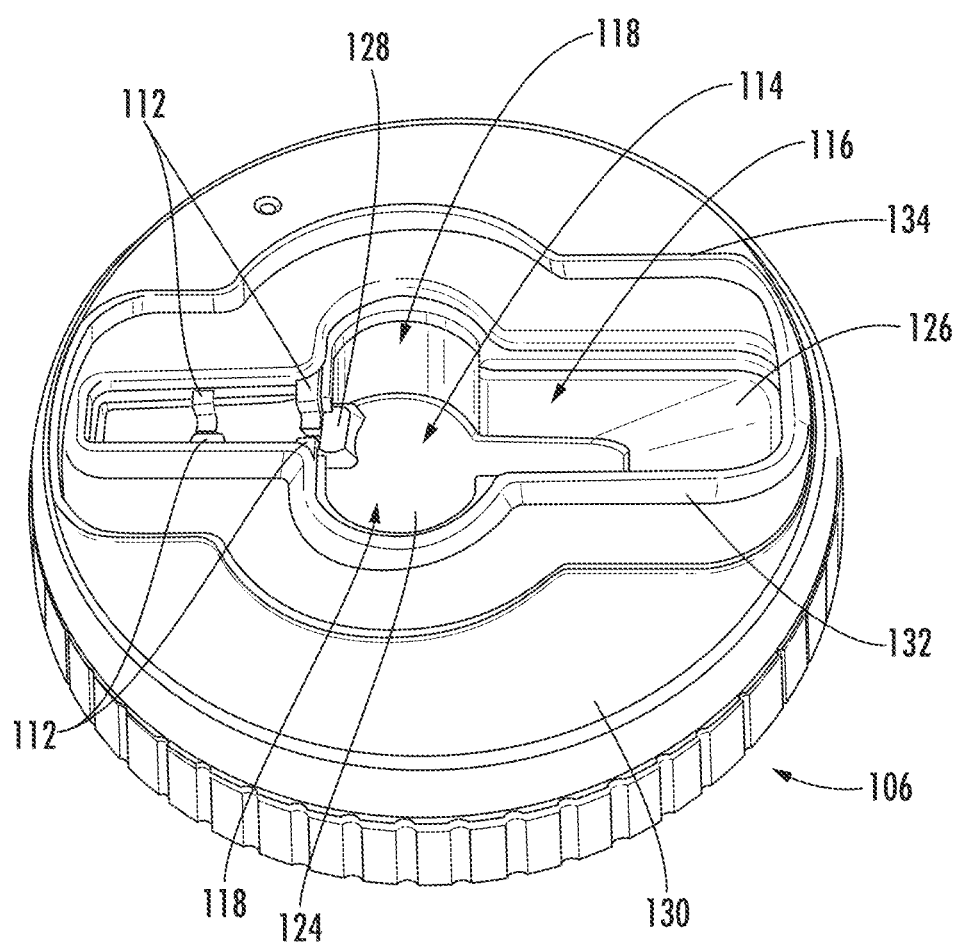
FIG. 9 shows an exemplary embodiment of a container for a tissue cartridge in accordance with the present disclosure.
Figure 10:
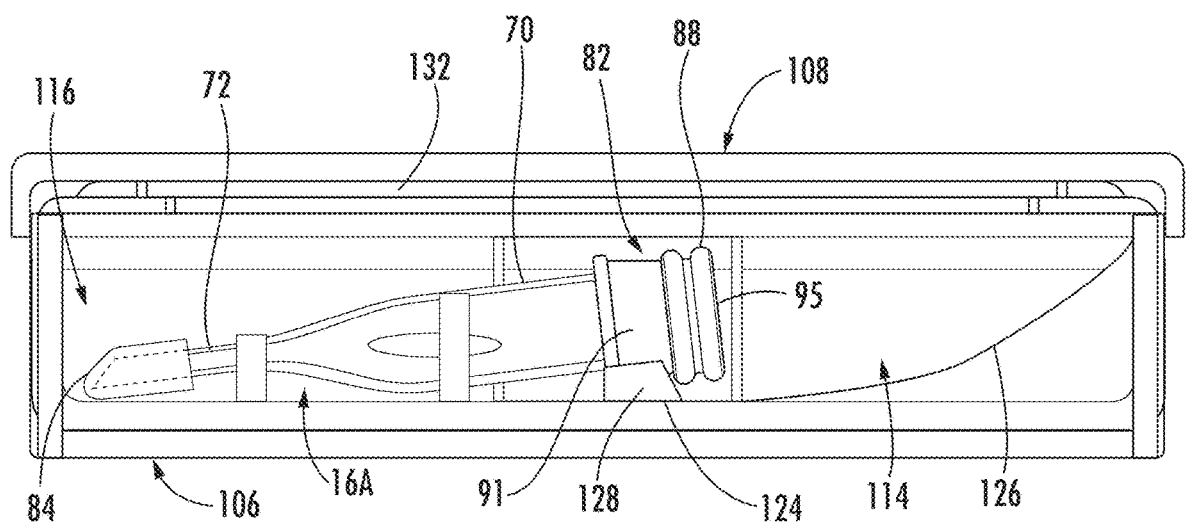
FIG. 10 shows a side view of the container of FIG. 9, in accordance with the present disclosure.
Figure 13:
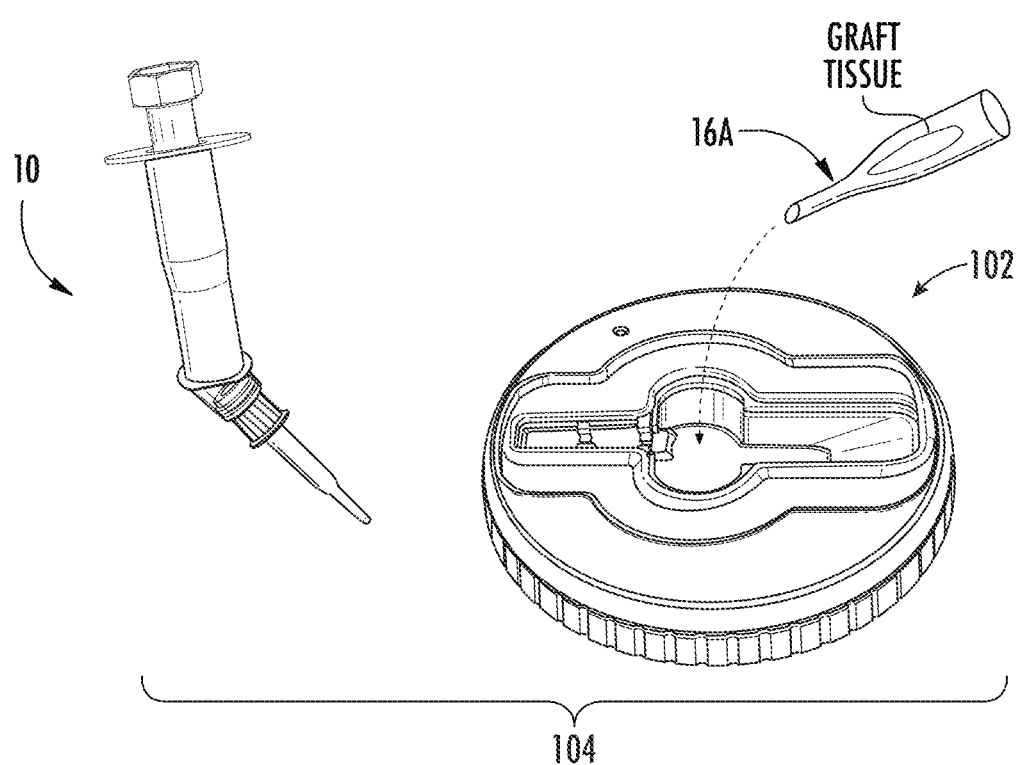
FIG. 13 shows a stylized view of an exemplary kit including an injector and a container having a pre-loaded tissue cartridge therein, in accordance with the present disclosure.

Referring now to FIGS. 9 and 10, a container 102 for a cartridge 16 is shown. FIG. 9 shows a perspective view of an exemplary embodiment of a container 102 and FIG. 10 shows a side view of the container 102 with a pre-loaded cartridge 16A therein. In one embodiment, the container 102 is sized and configured to receive and retain a cartridge 16, such as a pre-loaded cartridge 16A (that is, a cartridge 16 with graft tissue therein), and an amount of storage solution. Further, in one embodiment, the container 102 is a single-use container that, once opened, cannot be resealed. In another embodiment, the container 102 is a multi-use container that can be opened and resealed many times. In some embodiments, the container 102, with a pre-loaded cartridge 16A, and the injector 10 are sold together as a kit 104 (for example, as shown in FIG. 13). In other embodiments, the container 102, with or without a pre-loaded cartridge 16, is sold separately from the injector 10.

Continuing to refer to FIGS. 9 and 10, in one embodiment, the container 102 generally includes a base 106 and a lid 108 configured to coupled configured to be coupled to each other. The base 106 and the lid 108 together define a chamber within the container 102 that is sized and configured to hold a cartridge 16 (with or without a cartridge coupling element 82) and, optionally, a volume of preservation solution. In one embodiment, the container 102 also includes at least one cartridge retainment element 112 configured to prevent graft tissue from escaping a pre-loaded cartridge 16A during storage, shipping, and the like. Alternatively, in some embodiments, the container 102 may not include containment elements. In discussing FIGS. 9 and 10, references is made herein to a cartridge 16 for simplicity; however, it will be understood that an empty cartridge 16 or a pre-loaded cartridge 16A may be used.

Figure 11:
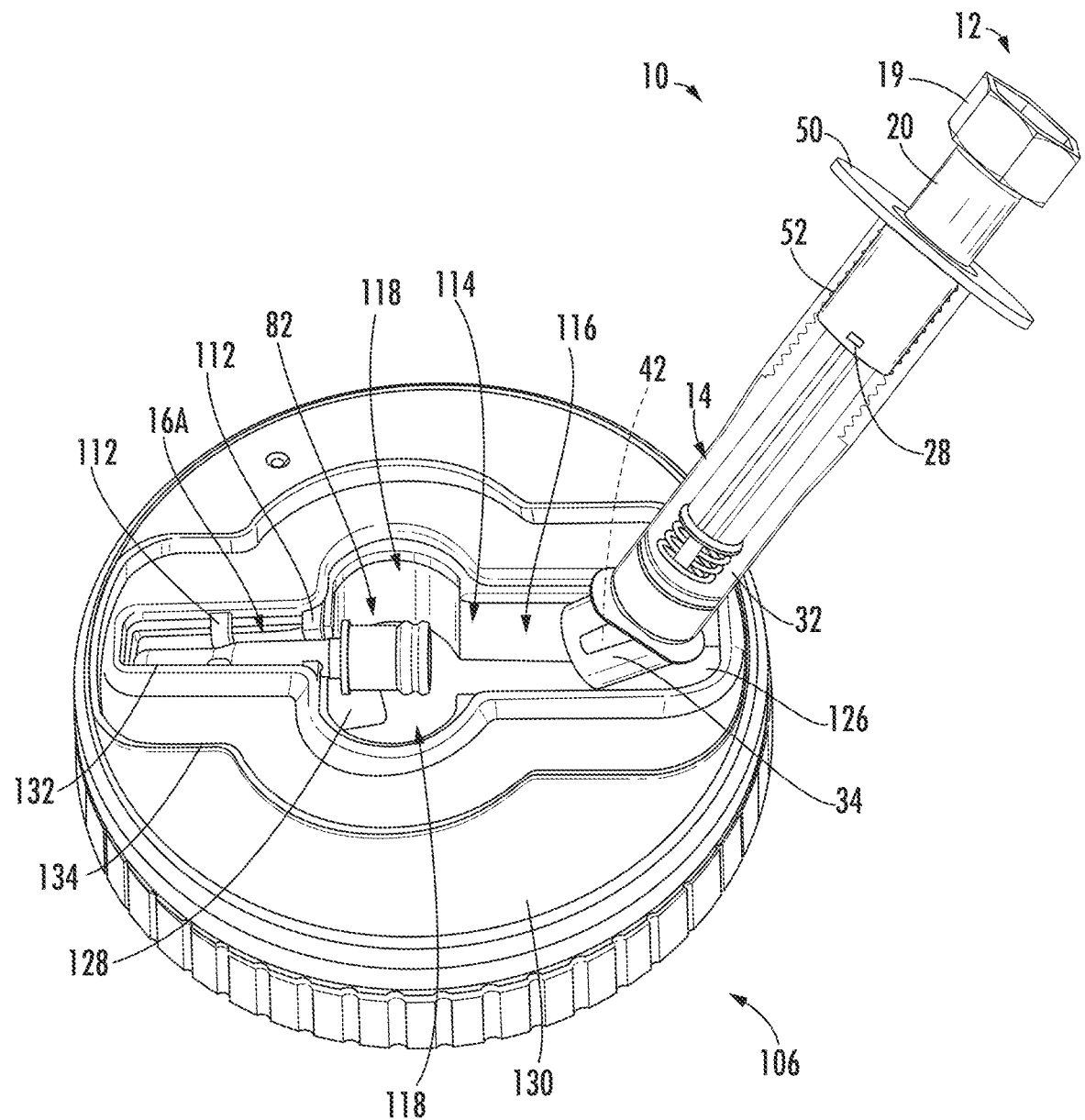
FIG. 11 shows an exemplary first step of coupling an injector to a tissue cartridge within a container, in accordance with the present disclosure.
Figure 12:
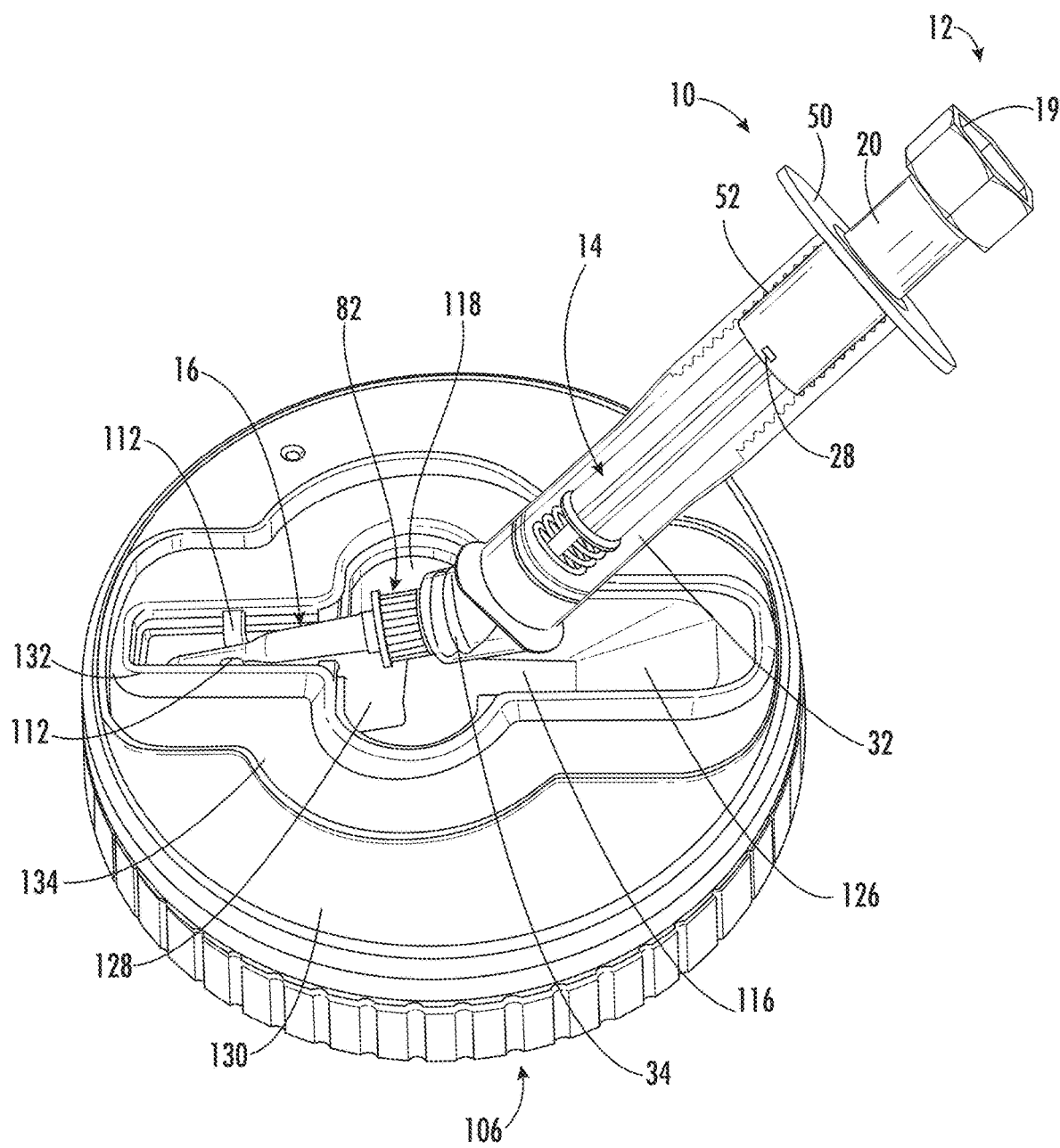
FIG. 12 shows an exemplary second step of coupling an injector to a tissue cartridge within a container, in accordance with the present disclosure.

Continuing to refer to FIGS. 9 and 10, in one embodiment, base 106 defines a well 114 that is sized and configured to retain a cartridge 16, without or without a cartridge coupling element 82, or other cartridge (for example, a Jones tube cartridge or other cartridge used for medical procedures). In one embodiment, the well 114 is a reservoir that has a first portion 116 with an elongate or at least substantially elongate shape. In some embodiments, the well 114 further includes at least one second portion 118, each optionally with a rounded shape, that extends away from the first portion 116. In one embodiment, the well 114 includes two opposite second portions 118 that extend away from the first portion 116. These second portions 118 are each sized and shaped to receive at least a portion of a user's finger, thereby allowing the user to easily grasp and remove the cartridge 16 from the first portion 116. For example, as is shown in FIGS. 11 and 12, at least a portion of the cartridge 16 (in some embodiments, at least a portion of the cartridge coupling element 82) extends along the first portion 116 to a location where the second portion(s) 118 meet the first portion 116, which makes it easy for the user to securely grasp the cartridge. In one embodiment, the first portion 116 includes a first end and a second end opposite the first end. In one embodiment, the first end includes one or more cartridge retainment elements 112 that are sized and configured to retain the cartridge 16 and prevent it from moving within the well 114 (to hold the cartridge 16 in place). In one embodiment, each cartridge retainment element 112 is a resilient tab that exerts a force against the cartridge 16 when the cartridge 16 is installed within the container 102. In one embodiment, the first end of the first portion 116 includes at least two opposite cartridge retainment elements 112 configured to exert opposing forces against the cartridge 16 to hold it in place. However, it will be understood that other suitable mechanisms may be used, such as rubber bumpers, rings that at least partially encircle the cartridge 16, or the like.

Continuing to refer to FIGS. 9 and 10, in one embodiment, the floor 124 of the well 114 at the second end of the first portion 116 is sloped to define a ramp 126, leading from a relatively shallower portion to a relatively deeper portion of the well 114 at a location between the first end and the second end, such as at a location that is proximate the second end or at a location that is at or proximate where the first end meets the second end. Put another way, the floor 124 is configured such that the well 114 becomes deeper moving in a direction from the second end toward the first end. Additionally, in one embodiment the first end includes a platform 128 that is sized and configured to support the cartridge 16 such that the first opening 76 and/or the opening 95 of the cartridge coupling element 82 is at a height that is aligned with the stalk 42 of the cylinder 14 when the cylinder 14 is inserted into the well 114 for coupling to the cartridge 16. As is described in greater detail below, this ramp 126 allows the user to slide the connection extension 34 of the cylinder 14 down into the well 114 and into contact with the cartridge 16 or cartridge coupling element 82. That is, the ramp 126 guides the cylinder 14 toward the cartridge 16 to facilitate rapid and secure connection between the cartridge 16 and the cylinder 14.

Continuing to refer to FIGS. 9 and 10, in one embodiment, the container 102 further includes an upper face 130 that includes an aperture that at least partially defines the well 114. In one embodiment, the well 114 extends downward from the upper face 130 (that is, away from the lid 108 when the lid 108 is coupled to the base 106). In one embodiment, the upper face 130 also includes a first fluid barrier 132, such as a ridge, lip, or gasket extending from the upper face 130, that completely surrounds the aperture of the upper face 130. The first fluid barrier 132 optionally follows the contours of the shape of the aperture of the upper face 130. In one embodiment, the upper face 130 also include a second fluid barrier 134, such as a ridge, lip, or gasket that has a maximum diameter that is greater than a maximum diameter of the first fluid barrier 132. Put another way, the second fluid barrier 134 completely surrounds the first fluid barrier 132. The second fluid barrier 134 optionally follows the contours of the shaper of the first fluid barrier 132. However, it will be understood that the first fluid barrier 132 and/or the second fluid barrier 134 may have any suitable size, shape, or configuration. In one embodiment, the base 106 and lid 108 are composed of a rigid or semi rigid material, such as plastic, glass, polymer, and/or metal. The base 106 and the lid 108 may be composed of the same or different materials. Further, at least a portion of the base 106 and/or at least a portion of the lid 108 may be transparent or translucent so a cartridge 16 therein is visible. In one embodiment, the upper face 130 is composed of the same material(s) as the base 106 and/or the lid 108. In another embodiment, at least a portion of the upper face 130, such as the first and second fluid barriers 132, 134, are composed of a resiliently compressible and/or deformable material, such as natural or synthetic rubber or rubberized material that allows the first and/or second fluid barriers 132, 134 to function as a gasket.

Continuing to refer to FIGS. 9 and 10, in one embodiment the well 114 is sized and configured to contain a volume of storage solution. For example, the well 114 may be sized and configured to hold approximately 20 mL (±10 mL) of storage solution when the cartridge 16 is inside the well. However, it will be understood that the base 106, the well 114, and/or other components of the container 102 may be sized and configured to contain any volume of solution needed for a particular procedure. In one embodiment, the first and second fluid barriers 132, 134 are in contact with the inner surface of the lid 108 when the lid 108 is coupled to the base 106. Thus, when the container 102 is closed, the storage solution within the well 114 is contained within the well, the first fluid barrier 132, and the lid 108, and cannot escape the well during storage and/or transport and air bubble entry is prevented. The second fluid barrier 134 may be sized, configured, and/or placed at a distance from the first fluid barrier 132 such that the volume of the area between the first fluid barrier 132 and the second fluid barrier 134 is sufficient to contain a volume of storage solution. For example, the volume of storage solution may be determined based on the fluid displacement caused by insertion of at least a portion of the body 32 of the cylinder 14 into the well 114 of the open container 102 when the cylinder 14 is coupled to the cartridge 16 (as discussed below regarding FIGS. 11 and 12.

Referring now to FIGS. 11 and 12, an exemplary method for coupling an injector 10 to a cartridge 16 within a container 102 is shown. FIG. 11 shows a first exemplary step in the method and FIG. 12 shows a second exemplary step in the method. As shown in FIG. 11, in one embodiment the lid 108 is removed from the base 106 to expose the cartridge 16 within the well 114. A volume of storage solution is contained within the well 114 by the first fluid barrier 132. In one embodiment, the user inserts the connection extension 34 of the cylinder 14 into the first end of the first portion 116 of the well 114, along the ramp 126 and toward the cartridge 16. In one embodiment, the cartridge 16 is coupled to a cartridge coupling element 82, and the connection extension 34 (and stalk 42) is advanced toward the opening 95 of the cartridge coupling element 82. As a portion of the cylinder 14 is inserted into the well, a corresponding volume of the storage solution is displaced out of the well 114 and at least some of which may pass over the first fluid barrier 132. Any fluid passing over the first fluid barrier 132 is contained by the second fluid barrier 134.

As is shown in FIG. 12, in one embodiment the cylinder 14 is advanced along the floor 124 of the well 114 until it is in contact with the cartridge 16. In one embodiment, the cylinder 14 is advanced until the friction fit element 88 passes into the connection extension 34 and the stalk 42 passes into the opening 95 of the friction fit element 88. The size and/or configuration of the friction fit element 88, the connection extension 34, and the stalk 42 allow secure coupling of the coupling of the cartridge coupling element 82 and the cylinder 14 by friction fit. Once the cartridge is coupled to the cylinder, the user then lifts the cylinder 14 away from the well 114 to disengage the cartridge 16 from the one or more cartridge retainment elements 112. In this manner, the user may easily couple the cartridge and the injector 10 with little or no struggle or error. The container 102 may then be discarded or cleaned and reused.

Referring now to FIG. 13, an exemplary kit 104 is shown, such as a kit for performing corneal transplant. In one embodiment, the kit 104 includes a container 102 with a pre-loaded cartridge 16A therein, and an injector 10. However, it will be understood that the kit 104 may, in some embodiments, include additional components and/or a cartridge 16A that is not pre-loaded (that is, a cartridge 16 that does not include graft tissue therein at the time of sale) or a cartridge, container, and/or injector other than those shown and described herein).

Figure 14:
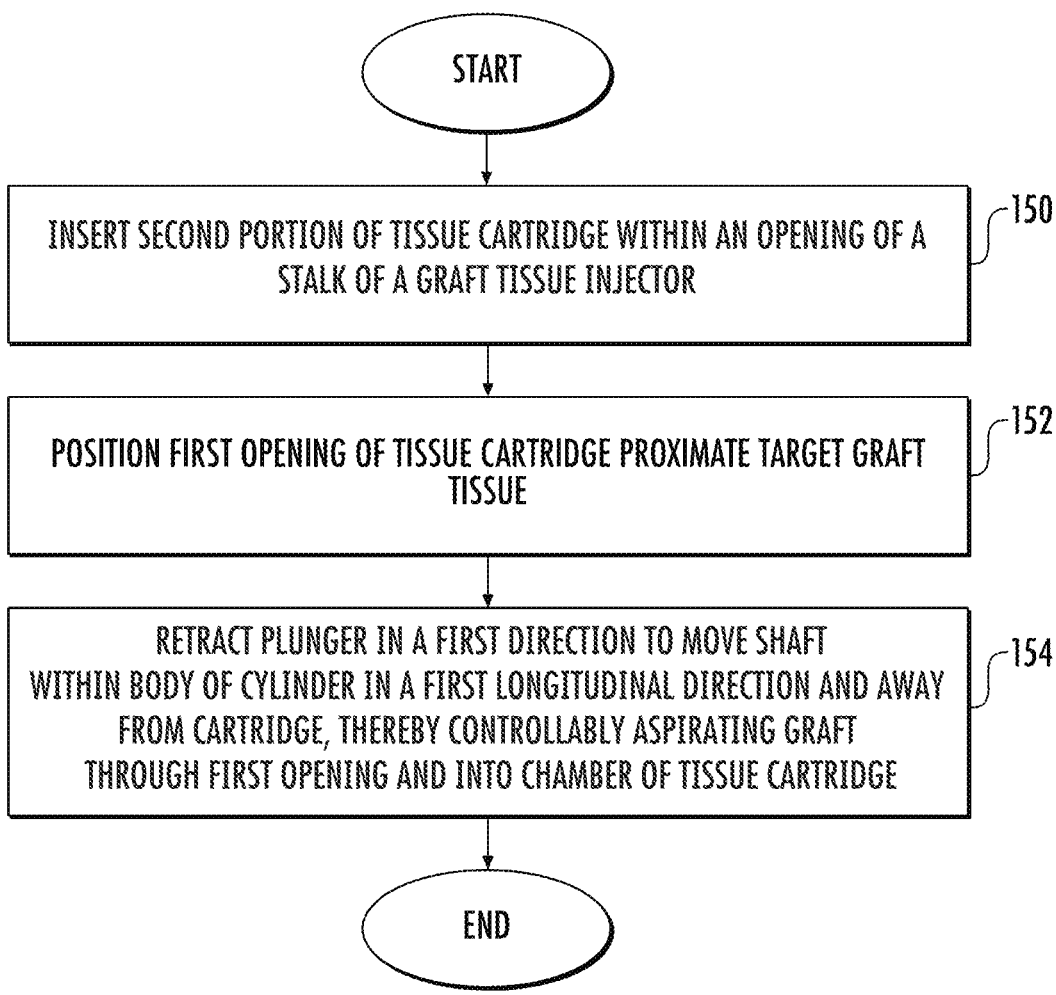
FIG. 14 shows an exemplary method of aspirating graft tissue into an injector in accordance with the present disclosure.
Figure 15:
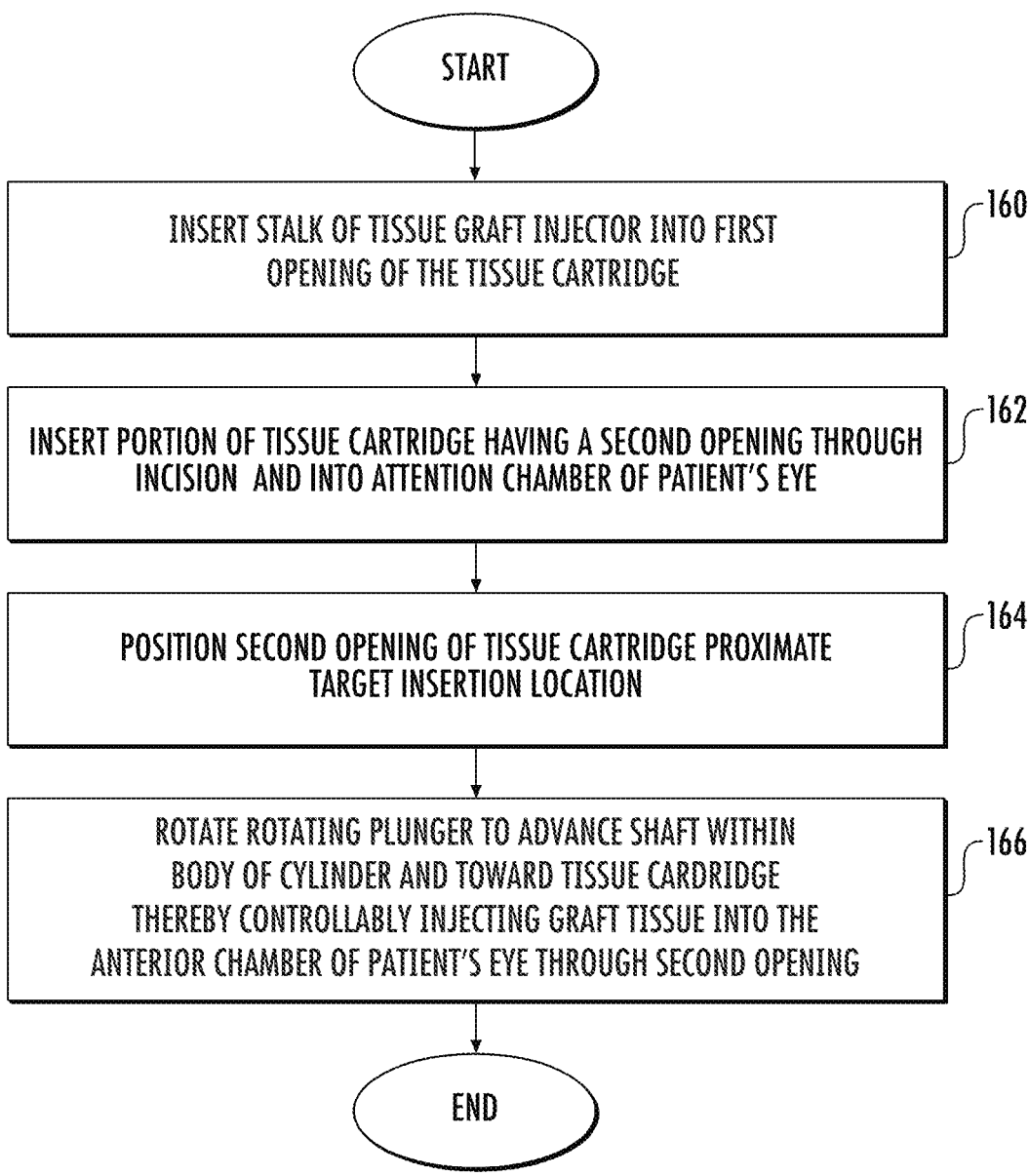
FIG. 15 shows an exemplary method of injecting graft tissue from an injector, in accordance with the present disclosure.

Referring now to FIGS. 14 and 15, exemplary methods of aspirating and delivering graft tissue to a delivery site is shown. In one embodiment, the single medical procedure may include a first method of aspirating graft tissue into an injector 10 (for example, as shown in FIG. 14) and a second method of then delivering or injecting the graft tissue from the injector 10 into or at the delivery site (for example, as shown in FIG. 15). In another embodiment, such as when the injector 10 is used with a pre-loaded tissue cartridge 16A, the medical procedure may include only a method of delivering or injecting the graft tissue from the injector 10 into or at the delivery site (for example, as shown in FIG. 15). Additionally, some medical procedures may require graft tissue to be manually placed inside the cartridge 16, rather than aspirating the graft tissue into the cartridge 16 with the injector 10. It will be understood that the methods of FIGS. 14 and 15 may be used for other medical procedures and/or biological materials, and are not limited to corneal transplant procedures. For example, intraocular lens insertion, pupil expansion device insertion, DSEK, ultrathin DSEK (UT-DSEK), nanothin DSEK (NT-DSEK), or bioengineered membrane endothelial keratoplasty Referring now to FIG. 14, an exemplary method of aspirating a graft tissue with the injector 10 is shown. The graft tissue may be contained within a volume of suitable solution, such as balanced saline solution (BSS) or similar fluid. In use, the injector 10 may be at least partially filled with a solution suitable for containing the graft tissue without damage, such as BSS. Further, before aspirating the graft tissue, the user ensures the plunger 12 is in a position such that the shaft 20 may be further retracted within the chamber 40 in a direction away from the cartridge 16. That is, the shaft 20 must be retracted within the chamber 40 in a direction opposite the cartridge 16 at least over a distance sufficient to aspirate the graft tissue. In one non-limiting example, the user ensures the shaft 20 is fully advanced within the chamber 40 of the body 32 such that the free end 26 of the shaft 20 is in contact with an inner surface of the end wall 54 and/or that the plunger 12 cannot be further advanced within the chamber 40 by. However, it will be understood that in some examples the shaft 20 is less than fully advanced.

Continuing to refer to FIG. 14, in a first step 150 the user engages the cartridge 16 with the connection extension 34 and stalk 42 of the cylinder 14 in a first or aspiration configuration. In one embodiment, the user inserts at least a portion of the second portion 72 of the cartridge 16 into the opening 45 of the stalk 42, thereby leaving the first portion 70, and the first opening 76, of the of the cartridge 16 available for aspirating fluid and graft tissue into the chamber 74 of the cartridge 16 (for example, as shown in FIG. 3). The first opening 76 is wider than the second opening 78, which may reduce the likelihood of graft tissue damage during aspiration.

Continuing to refer to FIG. 14, in a second step 152 the user positions the first opening 76 of the cartridge 16 proximate the graft tissue. In one non-limiting example, the graft tissue is a narrow, elongate Descemet's roll formed spontaneously after a circular layer of endothelium/Descemet's membrane is removed from the donor posterior stroma, and is stained with blue stain such as 0.06% trypan blue. To aspirate the graft tissue through the first opening 76 and into the chamber 74 in a third step 154, in one embodiment (for example, using the injector 10 of FIGS. 1-4) the user retracts the plunger 12 longitudinally (linearly), over a distance suitable to aspirate the graft tissue (and fluid). This distance may be any distance, and in one embodiment a maximum retraction distance is the point at which the protrusion 28 on the shaft 20 of the plunger 12 meets the threading 52 within the chamber 40 (that is, the user may stop retracting the plunger 12 when the protrusion 28 meets the threading 52). It will be noted that the plunger 12 may be longitudinally retracted without rotation, although some degree of rotation may, but does not necessarily, occur during use, as opposed to required rotation when the protrusion 28 is engaged with the threading 52. In other embodiments (for example, when the graft tissue has not yet been aspirated and/or it is desirable to aspirate more fluid), the user may retract the plunger longitudinally (linearly) until the protrusion 28 meets the threading 52, at which point the user then rotates (and may slowly rotate) the knob 19 of the plunger 12 in a first direction (for example, the counter-clockwise direction). Rotation of the knob 19 in the first direction retracts the shaft 20 slowly within the chamber 40 of the body 32 in a direction that is away from the cartridge 16. In one embodiment, the first opening 76 of the cartridge 16 is sized and configured such that the graft tissue may pass without resistance through the first opening 76 and into the chamber 74. Thus, upon aspiration of the graft tissue, the graft tissue is located within the chamber 74 of the cartridge 16 within BSS or similar fluid. In some embodiments, rotation of the plunger 12 allows the user to aspirate the graft tissue more slowly and with more precision and control than offered by currently known syringe-type injectors.

Referring now to FIG. 15, an exemplary method of injecting graft tissue from the injector 10 is shown. In some embodiments, the method of FIG. 15 begins after the method of FIG. 14 is performed. In other embodiments, such as when the injector 10 is used with a pre-loaded cartridge 16A, the user may simply begin the method of FIG. 15 by using the pre-loaded cartridge 16A. In any embodiment, the chamber 40 includes some volume of fluid (for example, BSS or other suitable solution), and may be completely full of fluid, and the graft tissue is within the cartridge 16. Thus, the plunger 12 may be in the fully retracted position at the onset of the method. In any embodiment, in a first step 160, the user engages the cartridge 16 (or, in some embodiments, the cartridge coupling element 82) with the connection extension 34 and the stalk 42 of the cylinder 14 in a second or injection configuration. To do this, the user inserts at least a portion of a connection end the cylinder 14 of the injector 10 into the well 114 of the container 102 (for example, the second end 38 of the cylinder 14 that includes the connection extension 34 and the stalk 42). In one embodiment, the user inserts at least a portion of the stalk 42 into the first opening 76 of the cartridge 16, thereby leaving the second portion 72, and the second opening 78, of the cartridge 16 free to insert into the patient's eye and deliver or inject the graft tissue (as shown in FIGS. 1 and 2). In other embodiments, the user inserts at least a portion of the stalk 42 into the opening 95 of the cartridge coupling element 82, thereby leaving the second portion 72, and the second opening 78, of the cartridge 16 free to insert into the patient's eye to deliver or inject the graft tissue.

Continuing to refer to FIG. 15, in a second step 162, at least a portion of the second portion 72 of the cartridge 16 (that is, the narrow tip of the cartridge 16) is inserted through an incision, such as a scleral or corneal incision, and into the anterior chamber of the patient's eye. In a third step 164, the second opening 78 of the cartridge 16 is positioned at a target delivery site within the anterior chamber. In a fourth step 166, in one embodiment (for example, using the injector 10 of FIGS. 1-4), with the protrusion 28 of the shaft 20 of the plunger 12 and the threading 52 within the chamber 40 engaged, the user slowly rotates the knob 19 of the plunger 12 in the second direction (for example, the clockwise direction), which advances the shaft 20 within the chamber 40 of the body 32 in a direction that is toward the cartridge 16, which in turn ejects the fluid and the graft tissue from the cartridge 16 and into the anterior chamber of the patient's eye. The rotation of the plunger 12 causes the plunger 12 to advance more slowly through the chamber 40 than if the protrusion 28 and the threading 52 were not mateably engaged. Further, the narrow diameter of the chamber 74 within the second portion 72 of the cartridge 16 may help align the graft tissue in the proper orientation for delivery to the target delivery site. Rotating the plunger 12 to advance the plunger 12 allows the user to inject the graft tissue into the anterior chamber more slowly and with more precision and control than offered by currently known syringe-type injectors. Additionally, injecting the graft tissue and fluid more slowly into the anterior chamber may help prevent over-pressurization of the anterior chamber during delivery.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. An injector kit, the injector kit comprising:
an injector including a body, the body including:
a first end having a first opening;
a second end opposite the first end, the second end having a second opening and an end wall at least partially defining the second opening;
a chamber extending from the first end to the second end, the chamber being in fluid communication with the first opening and the second opening, the chamber being at least partially defined by an inner surface of the body;
a stalk having a first end extending from the end wall of the second end of the body, a second end opposite the first end and having an opening, and a lumen therebetween, the lumen being in fluid communication with the chamber of the body of the injector and the opening of the second end of the stalk; and
a connection extension, the connection extension including a first end extending from the second end of the body, a second end opposite the first end, and an opening at least partially defined by the second end, and a chamber between the opening and the end wall of the second end of the body, the chamber of the connection extension having an inner surface, the stalk being located within the chamber of the connection extension, the stalk and the connection extension being coaxial, the inner surface of the chamber of the connection extension being without threading;
a cartridge coupling element, the cartridge coupling element having an external surface, the cartridge coupling element being removably engageable with the body of the injector and including:
a first portion including a friction fit element, at least a portion of the friction fit element being on the external surface of the cartridge coupling element, the friction fit element having an opening with a diameter, the friction fit element being sized and configured such that the portion of the friction fit element that is on the external surface of the cartridge coupling element is in contact with the inner surface of the connection extension when the cartridge coupling element is coupled to the injector, the friction fit element being removably couplable to the stalk of the body of the injector within the chamber of the connection extension solely by friction fit between the friction fit element and the inner surface of the chamber of the connection extension, the friction fit element being rotatable about an axis of the connection extension of the body of the injector within the connection extension when the cartridge coupling element is engaged with the body of the injector and the injector is in use, the friction fit element being composed of a resiliently compressible material; and
a second portion opposite the first portion, the second portion including a collar; and
a tissue cartridge, the collar of the cartridge coupling element being removably and securely engageable with the tissue cartridge to couple the tissue cartridge to the body of the injector.

2. The injector kit of claim 1, wherein the tissue cartridge includes:
a first portion defining a first opening;
a second portion defining a second opening, the second opening being opposite the first opening; and
a chamber between and in fluid communication with the first opening of the tissue cartridge and the second opening of the tissue cartridge,
the collar of the cartridge coupling element being removably engageable with the first portion of the tissue cartridge.

3. The injector kit of claim 2, wherein the collar of the cartridge coupling element is removably engageable with the first portion of the tissue cartridge by a luer lock.

4. The injector kit of claim 2, wherein an outer surface of the first portion of the tissue cartridge includes a first luer lock component and an inner surface of the collar includes a second luer lock component, the first and second luer lock components being matably engageable with each other to prevent a fluid from leaking between the tissue cartridge and cartridge coupling element.

5. The injector kit of claim 2, wherein:
the friction fit element is sized and configured to be at least partially received within and to fit in close tolerance within the chamber of the connection extension of the body of the injector;
the stalk of the body of the injector has an outer diameter that is slightly smaller than the diameter of the opening of the friction fit element, such that the stalk is removably insertable within the opening of the friction fit element and securable therein by friction fit when the friction fit element is at least partially received within the chamber of the connection extension; and
the opening of the stalk of the body of the injector has an inner diameter that is slightly larger than the outer diameter of the second portion of the tissue cartridge, such that the second portion of the tissue cartridge is removably insertable within the opening of the stalk and securable therein by friction fit when the cartridge coupling element is disengaged from the stalk.

6. The injector kit of claim 2, wherein the stalk of the body of the injector is sized and configured to be at least partially inserted into the first opening of the tissue cartridge.

7. The injector kit of claim 1, wherein at least a portion of the inner surface of the body of the injector defines a threading, the injector kit further comprising a plunger, the plunger including:
a shaft having a first portion and a second portion opposite the first portion, the second portion having a free end; and
a knob coupled to the first portion,
an outer surface of at least a portion of the first portion defining a protrusion, the protrusion being located a distance from the knob and being sized and configured to rotatably engage with the threading of the body,
the plunger being rotatably advanceable and linearly advanceable within the body and rotatably retractable and linearly retractable within the body.

8. The injector kit of claim 1, wherein the body has a first longitudinal axis and the connection extension has a second longitudinal axis that is different than the first longitudinal axis, the second longitudinal axis being oriented at an angle from the first longitudinal axis.

9. The injector kit of claim 8, wherein the angle is less than approximately 90°.

10. The injector kit of claim 8, wherein the angle is between approximately 22.5° and approximately 67.5°.

11. The injector kit of claim 1, further comprising a container, the container including:
a base, the base having an upper face and a well, the well being configured to contain a volume of liquid, the well including a first portion and at least one second portion extending away from the first portion, a first end of the first portion being sized and configured to retain the tissue cartridge and a second end of the first portion having a ramp, the ramp being sloped downward toward the first end of the first portion and configured to guide the body of the injector toward the tissue cartridge when the tissue cartridge is retained within the first end of the first portion; and a lid that is removably couplable to the base.

12. The injector kit of claim 11, wherein the upper face includes:

a first fluid barrier surrounding the well; and a second fluid barrier surrounding and being a distance from the first fluid barrier, the well and the first fluid barrier being configured to contain a first volume of solution, and the first fluid barrier and the second fluid barrier being configured to contain a second volume of solution therebetween, the second volume of solution being less than the first volume of solution.

13. The injector kit of claim 12, wherein the first volume of solution is approximately 20 mL.

\* \* \* \* \*